US012692517B2

(12) United States Patent
Lai et al.

(10) Patent No.: US 12,692,517 B2
(45) Date of Patent: Jul. 28, 2026

(54) CRISPR/Cas12F ENZYME AND SYSTEM

(71) Applicant: China Agricultural University, Beijing (CN)

(72) Inventors: Jinsheng Lai, Beijing (CN); Yingsi Zhou, Beijing (CN); Jinjie Zhu, Beijing (CN); Fei Yi, Beijing (CN); Xiangbo Zhang, Beijing (CN); Haiming Zhao, Beijing (CN); Weibin Song, Beijing (CN)

(73) Assignee: China Agricultural University, Beijing (CN)

( * ) Notice: Subject to any disclaimer, the term of this patent is extended or adjusted under 35 U.S.C. 154(b) by 1119 days.

(21) Appl. No.: 17/289,204

(22) PCT Filed: Oct. 29, 2019

(86) PCT No.: PCT/CN2019/113996
§ 371 (c)(1),
(2) Date: Apr. 27, 2021

(87) PCT Pub. No.: WO2020/088450
PCT Pub. Date: May 7, 2020

(65) Prior Publication Data
US 2021/0395784 A1 Dec. 23, 2021

(30) Foreign Application Priority Data

Oct. 29, 2018 (CN) .......................... 201811266209.7

(51) Int. Cl.
| | |
|---|---|
| *C12N 15/90* | (2006.01) |
| *C12N 9/22* | (2006.01) |
| *C12N 15/11* | (2006.01) |
| *C12N 15/62* | (2006.01) |

(52) U.S. Cl.
CPC ............. *C12N 15/902* (2013.01); *C12N 9/22* (2013.01); *C12N 15/111* (2013.01); *C12N 15/62* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 10,808,245 | B2 * | 10/2020 | Chong ..................... | C12N 9/22 |
| 2021/0395784 | A1 * | 12/2021 | Lai ....................... | C12N 15/902 |

OTHER PUBLICATIONS

Bowie et al., Deciphering the Message in Protein Sequences: Tolerance to Amino Acid Substitutions, Science, 1990, 247:1306-1310 (Year: 1990).*
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Biol. 111:2129-2138, 1990 (Year: 1990).*
Lazar et al., Transforming Growth Factor ox: Mutation of Aspartic Acid 47 and Leucine 48 Results in Different Biological Activities, Mol. Cell. Biol., 8:1247-1252, 1988 (Year: 1988).*
Bork, Powers and pitfalls in sequence analysis: the 70% hurdle, Genome Research, 2000, 10:398-400 (Year: 2000).*
Adler et al., Nucleic Acids Research, 52 (D1): D590-D596, Publication Date: Dec. 27, 2023 (Year: 2023).*
Drake et al., Genetics, 148, 1667-1686, Publication Year: 1998 (Year: 1998).*

* cited by examiner

*Primary Examiner* — Samira J Jean-Louis
*Assistant Examiner* — Cheng Lu
(74) *Attorney, Agent, or Firm* — Bayramoglu Law Offices LLC

(57) ABSTRACT

The application belongs to the field of nucleic acid editing, in particular to the field of clustered regularly interspaced short palindromic repeats (CRISPR) technology. In particular, the application provides a Cas effector protein, a fusion protein with the Cas effector protein, and a nucleic acid molecule encoding the same. Also provided are a compound and a composition for nucleic acid editing (e.g., gene or genome editing) with the protein or the nucleic acid molecule, and a method for nucleic acid editing (e.g., gene or genome editing) using the protein.

6 Claims, 3 Drawing Sheets

Specification includes a Sequence Listing.

SEQ ID NO: 13          SEQ ID NO: 14          SEQ ID NO: 15

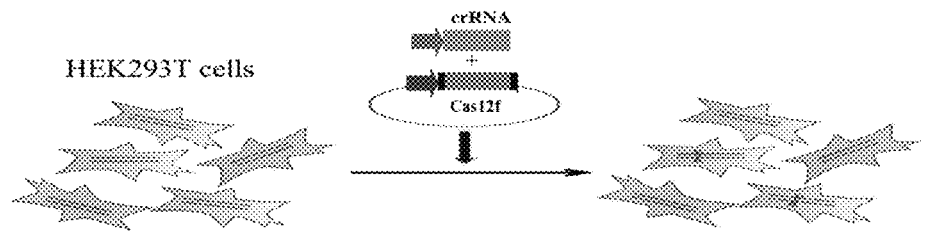
Figure 3a
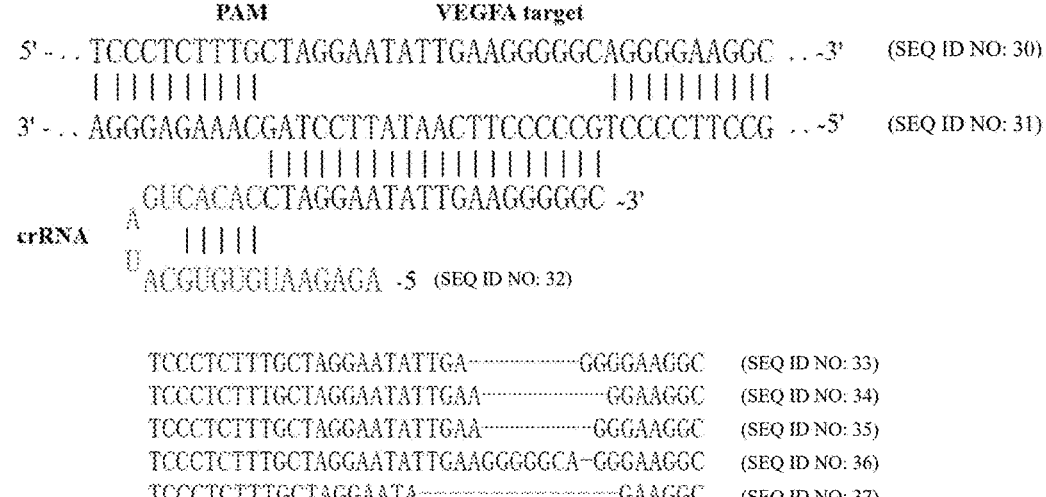
```
TCCCTCTTTGCTAGGAATATTGA----------GGGGAAGGC    (SEQ ID NO: 33)
TCCCTCTTTGCTAGGAATATTGAA-----------GGAAGGC    (SEQ ID NO: 34)
TCCCTCTTTGCTAGGAATATTGAA----------GGGAAGGC    (SEQ ID NO: 35)
TCCCTCTTTGCTAGGAATATTGAAGGGGGCA-GGGAAGGC      (SEQ ID NO: 36)
TCCCTCTTTGCTAGGAATA--------------GAAGGC       (SEQ ID NO: 37)
```
Figure 3b
| | target gene | number of indels | total number of Read (Total Read) | editing efficiency |
|---|---|---|---|---|
| Cas12f.4 | VEGFA | 4,571 | 108,873 | 4.20% |
| Cas12f.5 | VEGFA | 549 | 176,723 | 0.31% |
| Cas12f.6 | VEGFA | 390 | 202,251 | 0.19% |
Figure 3c

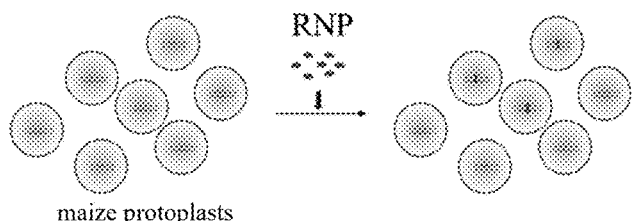

maize protoplasts

Figure 4a

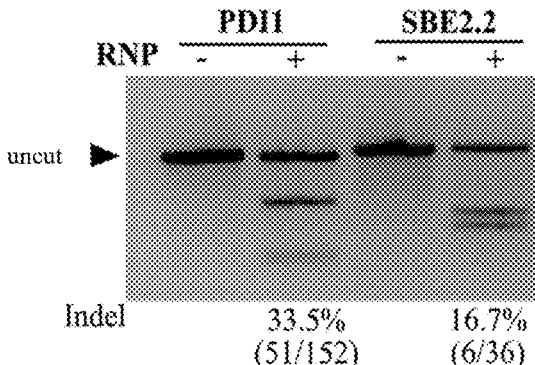

| | PDI1 | | SBE2.2 | |
|---|---|---|---|---|
| RNP | - | + | - | + | uncut ►

Indel          33.5%              16.7%
              (51/152)           (6/36)

Figure 4b

PDI1 target

5' - CTTGATTTCCTTGTCCTTGAATTCCTCCGCGGCAGCAGAGTAGGCAG -3'   Indel   (SEQ ID NO: 38)

| | Indel | |
|---|---|---|
| CTTGATTTCCTTGTCCTTGA············CAGCAGAGTAGGCAG | -12 | (SEQ ID NO: 39) |
| CTTGATTTCCTTGTCCTTGAATT···········CAGCAGAGTAGGCAG | -9 | (SEQ ID NO: 40) |
| CTTGATTTCCTTGTCCTTGAATT··········CGGCAGCAGAGTAGGCAG | -6 | (SEQ ID NO: 41) |
| CTTGATTTCCTTGTCCTTGAAT········TCCGCGGCAGCAGAGTAGGCAG | -3 | (SEQ ID NO: 42) |
| CTTGATTTCCTTGTCCTTGAA·············AGAGTAGGCAG | -15 | (SEQ ID NO: 43) |
| CTTGATTTCCTTGTCCTTGA··············AGAGTAGGCAG | -18 | (SEQ ID NO: 44) |
| CTTGATTTCCTTGTCCTTGAATT···········CAGCAGAGTAGGCAG | -9 | (SEQ ID NO: 40) |
| CTTGATTTCCTTGT··················GCAGAGTAGGCAG | -20 | (SEQ ID NO: 45) |
| CTTGATTTCCTTGTCCTTGAA············GCAGAGTAGGCAG | -13 | (SEQ ID NO: 46) |
| CTTGATTTCCTTGTCCTT···············AGAGTAGGCAG | -18 | (SEQ ID NO: 47) |

SBE2.2 target

5' - GGCCTTTTCGGTGGATTTAGTCGGCTTGATCATGATGCCGAGTACTT -3'   Indel   (SEQ ID NO: 48)

| | Indel | |
|---|---|---|
| GGCCTTTTCGGTGGATTTAGTCG················ATGCCGAGTACTT | -11 | (SEQ ID NO: 49) |
| GGCCTTTTCGGTGGATTTAGTC··············GATGCCGAGTACTT | -11 | (SEQ ID NO: 50) |
| GGCCTTTTCGGTGGATTTA··················ATGATGCCGAGTACTT | -12 | (SEQ ID NO: 51) |
| GGCCTTTTCGGTGGATTTAGTC················ATGCCGAGTACTT | -12 | (SEQ ID NO: 52) |
| GGCCTTTTCGGTGGATTTAA··················ATGCCGAGTACTT | -14 | (SEQ ID NO: 53) |
| GGCCTTTTCGGTGGATTT····················GCCGAGTACTT | -18 | (SEQ ID NO: 54) |

Figure 4c

CRISPR/Cas12F ENZYME AND SYSTEM

CROSS-REFERENCE TO RELATED APPLICATIONS

This application is a Section 371 of International Application No. PCT/CN2019/113996, filed Oct. 29, 2019, which was published in the Chinese language on May 7, 2020 under International Publication No. WO 2020/088450 A1, which claims priority under 35 U.S.C. § 119(b) to Chinese Application No. 201811266209.7, filed Oct. 29, 2018, the disclosures of which are incorporated herein by reference in their entirety.

REFERENCE TO SEQUENCE LISTING SUBMITTED ELECTRONICALLY

This application contains a sequence listing, which is submitted electronically as an ASCII formatted sequence listing with a file name "Replacement_Sequence_Listing_688457.0083", creation date of Dec. 6, 2024, and having a size of 86,016 bytes. The sequence listing submitted electronically is part of the specification and is herein incorporated by reference in its entirety.

TECHNICAL FIELD

The present invention relates to the field of nucleic acid editing, in particular to the technical field of clustered regularly interspaced short palindromic repeats (CRISPR). Specifically, the present invention relates to Cas effector proteins, fusion proteins containing such proteins, and nucleic acid molecules encoding them. The present invention also relates to complexes and compositions for nucleic acid editing (for example, gene or genome editing), which comprise the proteins or fusion proteins of the present invention, or nucleic acid molecules encoding them. The present invention also relates to a method for nucleic acid editing (for example, gene or genome editing), using that comprising the proteins or fusion proteins of the present invention.

BACKGROUND

CRISPR/Cas technology is a widely used gene editing technology. It uses RNA guidance to specifically bind to target sequences on the genome and cut DNA to produce double-strand breaks and uses biological non-homologous end joining or homologous recombination for site-directed gene editing.

The CRISPR/Cas9 system is the most commonly used type II CRISPR system. It recognizes the PAM motif of 3'-NGG and cuts the target sequence with blunt ends. The CRISPR/Cas Type V system is a type of CRISPR system newly discovered in the past two years. It has a 5'-TTN motif and cuts the target sequence with sticky ends, such as Cpf1, C2c1, CasX, and CasY. However, the currently existing different CRISPR/Cas have different advantages and disadvantages. For example, Cas9, C2c1 and CasX all require two RNAs for guide RNA, while Cpf1 only requires one guide RNA and can be used for multiple gene editing. CasX has a size of 980 amino acids, while the common Cas9, C2c1, CasY and Cpf1 are usually around 1300 amino acids in size. In addition, the PAM sequences of Cas9, Cpf1, CasX, and CasY are more complex and diverse, and C2c1 recognizes the strict 5'-TTN, so that its target site is easier to be predicted than other systems, thereby reducing potential off-target effects.

In a word, given that the currently available CRISPR/Cas systems are limited by some shortcomings, the development of a more robust new CRISPR/Cas system with good performance in many aspects is of great significance to the development of biotechnology.

SUMMARY OF THE INVENTION

After a lot of experiments and repeated explorations, the inventor of the present invention has unexpectedly discovered a new type of RNA-guided endonuclease. Based on this discovery, the present inventor has developed a new CRISPR/Cas system and a gene editing method based on the system.

Cas Effector Protein

Therefore, in the first aspect, the present invention provides a protein having an amino acid sequence as shown in SEQ ID NO: 1, or having an amino acid sequence having at least 90%, at least 91%, at least 92%, at least 93%, at least 94%, at least 95%, at least 96%, at least 97%, at least 98%, or at least 99% sequence identity compared to SEQ ID NO: 1, the amino acid sequence substantially retains the biological function of SEQ ID NO:1.

In certain embodiments, the present invention provides a protein having an amino acid sequence as shown in SEQ ID NO:1 or an ortholog, homolog or variant thereof; wherein the ortholog, homolog or variant has at least 90%, at least 91%, at least 92%, at least 93%, at least 94%, at least 95%, at least 96%, at least 97%, at least 98%, or at least 99% sequence identity compared to SEQ ID NO:1, and substantially retains the biological function of SEQ ID NO:1.

In the present invention, the biological function of the above sequence includes, but is not limited to, the activity of binding to guide RNA, endonuclease activity, and the activity of binding to and cleaving a specific site of the target sequence guided by the guide RNA.

In certain embodiments, the protein is an effector protein in the CRISPR/Cas system.

In certain embodiments, the protein of the present invention has an amino acid sequence as shown in SEQ ID NO:1.

Derived Protein

The protein of the present invention can be subjected to derivatization, for example, linked to another molecule (for example, another polypeptide or protein). Generally, the derivatization of the protein (for example, labeling) will not adversely affect the desired activity of the protein (for example, the activity of binding to the guide RNA, endonuclease activity, the activity of binding to and cleaving a specific site of the target sequence guided by the guide RNA). Therefore, the protein of the present invention is also intended to include such derivatized forms. For example, the protein of the present invention can be functionally linked (through chemical coupling, gene fusion, non-covalent linkage or other means) to one or more other molecular groups, such as another protein or polypeptide, detection reagent, pharmaceutical reagent and the like.

In particular, the protein of the present invention can be connected to other functional units. For example, it can be linked to a nuclear localization signal (NLS) sequence to improve the ability of the protein of the present invention to enter the cell nucleus. For example, it can be connected to a targeting moiety to make the protein of the present invention have the targeting. For example, it can be linked to a detectable label to facilitate detection of the protein of the present invention. For example, it can be linked to an epitope tag to facilitate the expression, detection, tracing and/or purification of the protein of the present invention.

Conjugate

Therefore, in a second aspect, the present invention provides a conjugate comprising the above-mentioned protein and a modified portion.

In certain embodiments, the modified portion is selected from an additional protein or polypeptide, a detectable label, and any combinations thereof.

In certain embodiments, the additional protein or polypeptide is selected from an epitope tag, a reporter gene sequence, a nuclear localization signal (NLS) sequence, a targeting moiety, a transcription activation domain (such as, VP64), a transcription repression domain (for example, KRAB domain or SID domain), a nuclease domain (for example, Fok1), a domain having an activity selected from: nucleotide deaminase, methylase activity, demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity, and nucleic acid binding activity; and any combinations thereof.

In certain embodiments, the conjugate of the present invention comprises one or more NLS sequences, such as the NLS of the SV40 virus large T antigen. In certain exemplary embodiments, the NLS sequence is shown in SEQ ID NO: 19. In certain embodiments, the NLS sequence is located at, near, or close to the terminal (such as, N-terminal or C-terminal) of the protein of the present invention. In certain exemplary embodiments, the NLS sequence is located at, near, or close to the C-terminus of the protein of the present invention.

In certain embodiments, the conjugate of the present invention comprises an epitope tag. Such epitope tags are well known to those skilled in the art, examples of which include, but are not limited to, His, V5, FLAG, HA, Myc, VSV-G, Trx, etc., and those skilled in the art know how to select a suitable epitope tag according to the desired purpose (for example, purification, detection or tracing).

In certain embodiments, the conjugate of the present invention comprises a reporter gene sequence. Such reporter genes are well known to those skilled in the art, and examples of which include, but are not limited to GST, HRP, CAT, GFP, HcRed, DsRed, CFP, YFP, BFP and the like.

In certain embodiments, the conjugate of the present invention comprises a domain capable of binding to DNA molecules or intracellular molecules, such as maltose binding protein (MBP), DNA binding domain (DBD) of Lex A, DBD of GAL4, etc.

In certain embodiments, the conjugate of the present invention comprises a detectable label, such as a fluorescent dye, e.g., FITC or DAPI.

In certain embodiments, the protein of the present invention is optionally coupled, conjugated or fused to the modified portion via a linker.

In certain embodiments, the modified portion is directly connected to the N-terminus or C-terminus of the protein of the present invention.

In certain embodiments, the modified portion is connected to the N-terminus or C-terminus of the protein of the present invention through a linker. Such linkers are well known in the art, examples of which include, but are not limited to, a linker containing one or more (for example, 1, 2, 3, 4, or 5)

amino acids (such as, Glu or Ser) or amino acid derivatives (such as, Ahx, β-Ala, GABA or Ava) or PEG and the like.

Fusion Protein

In a third aspect, the present invention provides a fusion protein comprising the protein of the present invention and an additional protein or polypeptide.

In certain embodiments, the additional protein or polypeptide is selected from an epitope tag, a reporter gene sequence, a nuclear localization signal (NLS) sequence, a targeting moiety, a transcription activation domain (such as, VP64), a transcription repression domain (for example, KRAB domain or SID domain), a nuclease domain (for example, Fok1), a domain having an activity selected from: a nucleotide deaminase, methylase activity, a demethylase, transcription activation activity, transcription inhibition activity, transcription release factor activity, histone modification activity, nuclease activity, single-stranded RNA cleavage activity, double-stranded RNA cleavage activity, single-stranded DNA cleavage activity, double-stranded DNA cleavage activity, and nucleic acid binding activity; and any combinations thereof.

In certain embodiments, the fusion protein of the present invention comprises one or more NLS sequences, such as the NLS of the SV40 virus large T antigen. In certain embodiments, the NLS sequence is located at, near, or close to the terminal (such as, N-terminal or C-terminal) of the protein of the present invention. In certain exemplary embodiments, the NLS sequence is located at, near, or close to the C-terminus of the protein of the present invention.

In certain embodiments, the fusion protein of the present invention comprises an epitope tag.

In certain embodiments, the fusion protein of the present invention comprises a reporter gene sequence.

In certain embodiments, the fusion protein of the present invention contains a domain capable of binding to DNA molecules or intracellular molecules.

In certain embodiments, the protein of the present invention is optionally fused to the additional protein or polypeptide via a linker.

In certain embodiments, the additional protein or polypeptide is directly linked to the N-terminus or C-terminus of the protein of the present invention.

In certain embodiments, the additional protein or polypeptide is connected to the N-terminus or C-terminus of the protein of the present invention via a linker.

In certain exemplary embodiments, the fusion protein of the present invention has an amino acid sequence as shown in SEQ ID NO: 20.

The protein of the present invention, the conjugate of the present invention, or the fusion protein of the present invention is not limited by the manner in which it is produced. For example, it can be produced by genetic engineering methods (recombinant technology), or can be produced by chemical synthesis methods.

Direct Repeat

In a fourth aspect, the present invention provides an isolated nucleic acid molecule comprising a sequence selected from the following or consisting of a sequence selected from the following:

(i) a sequence as shown in SEQ ID NO: 7 or 13;

(ii) compared with the sequence as shown in SEQ ID NO: 7 or 13, a sequence having one or more base substitutions, deletions or additions (for example, 1, 2, 3, 4, 5, 6, 7, 8, 9 or 10 base substitutions, deletions or additions);

(iii) a sequence having at least 20%, at least 30%, at least 40%, at least 50%, at least 60%, at least 70%, at least 80%, at least 90%, at least 95% sequence identity with the sequence as shown in SEQ ID NO:7 or 13;

(iv) a sequence that hybridizes to the sequence as described in any one of (i) to (iii) under stringent conditions; or (v) a complementary sequence of the sequence as described in any one of (i)-(iii);

In addition, the sequence as described in any one of (ii)-(v) substantially retains the biological function of the sequence from which it is derived, and the biological function of the sequence refers to its activity as a direct repeat sequence in the CRISPR-Cas system.

In certain embodiments, the isolated nucleic acid molecule is a direct repeat sequence in the CRISPR-Cas system.

In certain embodiments, the nucleic acid molecule comprises a sequence selected from the following, or consists of a sequence selected from the following:

(a) a nucleotide sequence as shown in SEQ ID NOs: 7 or 13;

(b) a sequence that hybridizes to the sequence as described in (a) under stringent conditions; or (c) a complementary sequence of the nucleotide sequence as shown in SEQ ID NO: 7 or 13.

In certain embodiments, the isolated nucleic acid molecule is RNA.

CRISPR/Cas Complex

In a fifth aspect, the present invention provides a complex comprising:

(i) a protein component, which is selected from: the protein, conjugate or fusion protein of the present invention, and any combinations thereof; and (ii) a nucleic acid component, which comprises the isolated nucleic acid molecule as described in the fourth aspect and a targeting sequence capable of hybridizing to the target sequence from 5' to 3' direction, wherein the protein component and the nucleic acid component combine with each other to form a complex.

In certain embodiments, the targeting sequence is attached to the 3' end of the nucleic acid molecule.

In certain embodiments, the targeting sequence comprises the complementary sequence of the target sequence.

In certain embodiments, the nucleic acid component is a guide RNA in the CRISPR-Cas system.

In certain embodiments, the nucleic acid molecule is RNA.

In certain embodiments, the complex does not comprise trans-activating crRNA (tracrRNA).

In certain embodiments, the targeting sequence is at least 5, at least 10 in length. In certain embodiments, the targeting sequence is 10-30, or 15-25, or 15-22, or 19-25, or 19-22 nucleotides in length.

In certain embodiments, the isolated nucleic acid molecule is 55-70 nucleotides in length, such as 55-65 nucleotides, such as 60-65 nucleotides, such as 62-65 nucleosides, such as 63-64 nucleotides. In certain embodiments, the isolated nucleic acid molecule is 15-30 nucleotides in length, such as 15-25 nucleotides, such as 20-25 nucleotides, such as 22-24 nucleotides, such as 23 nucleotides.

In a specific embodiment, the present invention provides a CRISPR-Cas system, which comprises:

a) a guide RNA, which contains a direct repeat sequence and a guide sequence capable of hybridizing to the target sequence from 5' to 3' direction, and b) a Cas12f effector protein;

the guide RNA forms a complex with the Cas12f effector protein;

wherein the Cas12f protein has a size of 900-1200 amino acids, and there is a RuvC domain near its C-terminus, which is composed of RuvC-I, RuvC-II and RuvC-III motifs;

wherein the Cas12f is located within 500 bp of the CRISPR locus in the bacterial genome;

preferably, the length of the direct repeat sequence is 21 nt-36 nt, the length of the targeting sequence is 1-80 nt, and the last 16 or 17 bases of the direct repeat sequence can form a stem loop, the loop size is 8 or 9 nt, and the stem is composed of five pairs of complementary bases.

Encoding Nucleic Acid, Vector and Host Cell

In a sixth aspect, the present invention provides an isolated nucleic acid molecule comprising:

(i) a nucleotide sequence encoding the protein or fusion protein of the present invention;

(ii) encoding the isolated nucleic acid molecule as described in the fourth aspect; or (iii) a nucleotide sequence containing (i) and (ii).

In certain embodiments, the nucleotide sequence described in any one of (i) to (iii) is codon optimized for expression in prokaryotic cells. In certain embodiments, the nucleotide sequence as described in any one of (i) to (iii) is codon optimized for expression in eukaryotic cells.

In a seventh aspect, the present invention also provides a vector comprising the isolated nucleic acid molecule as described in the sixth aspect. The vector of the present invention can be a cloning vector or an expression vector. In certain embodiments, the vector of the present invention is, for example, a plasmid, a cosmid, a bacteriophage, a cosmid and the like. In certain preferred embodiments, the vector is capable of expressing the protein, fusion protein of the present invention, isolated nucleic acid molecule according to the fourth aspect or the complex according to the fifth aspect in a subject (for example, a mammal, such as a human).

In an eighth aspect, the present invention also provides a host cell containing the isolated nucleic acid molecule or vector as described above. Such host cells include, but are not limited to, prokaryotic cells such as *E. coli* cells, and eukaryotic cells such as yeast cells, insect cells, plant cells and animal cells (such as mammalian cells, e.g., mouse cells, human cells, etc.). The cells of the present invention can also be cell lines, such as 293T cells.

Composition and Vector Composition

In a ninth aspect, the present invention also provides a composition, which comprises:

(i) a first component, which is selected from: the protein, conjugate, fusion protein of the present invention, nucleotide sequence encoding the protein or fusion protein, and any combinations thereof; and (ii) a second component, which is a nucleotide sequence containing a guide RNA, or a nucleotide sequence encoding the nucleotide sequence containing a guide RNA;

wherein the guide RNA includes a direct repeat sequence and a targeting sequence from the 5' to 3', and the targeting sequence can hybridize with the target sequence;

the targeting RNA can form a complex with the protein, conjugate or fusion protein as described in (i).

In certain embodiments, the direct repeat sequence is an isolated nucleic acid molecule as defined in the fourth aspect.

In certain embodiments, the targeting sequence is connected to the 3' end of the direct repeat sequence. In certain embodiments, the targeting sequence comprises the complementary sequence of the target sequence.

In certain embodiments, the composition does not include tracrRNA.

In certain embodiments, the composition is non-naturally occurring or modified. In certain embodiments, at least one component of the composition is non-naturally occurring or modified. In certain embodiments, the first component is non-naturally occurring or modified; and/or, the second component is non-naturally occurring or modified.

In certain embodiments, when the target sequence is DNA, the target sequence is located at the 3' end of the protospacer adjacent motif (PAM), and the PAM has a sequence shown by 5'-TTN, wherein N is selected from A, G, T, and C. In certain embodiments, N is selected from A, T, and C.

In certain embodiments, when the target sequence is RNA, the target sequence does not have PAM domain restrictions.

In certain embodiments, the target sequence is a DNA or RNA sequence derived from a prokaryotic cell or a eukaryotic cell. In certain embodiments, the target sequence is a non-naturally occurring DNA or RNA sequence.

In certain embodiments, the target sequence is present in the cell. In certain embodiments, the target sequence is present in the cell nucleus or in the cytoplasm (such as, organelles). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminus or C-terminus of the protein. In certain embodiments, the NLS sequence is fused to the N-terminus or C-terminus of the protein.

In a tenth aspect, the present invention also provides a composition comprising one or more vectors, comprising:

(i) a first nucleic acid, which is a nucleotide sequence encoding a protein or fusion protein of the present invention; optionally, the first nucleic acid is operationally linked to a first regulatory element; and (ii) a second nucleic acid, which encodes a nucleotide sequence comprising a guide RNA; optionally the second nucleic acid is operationally linked to a second regulatory element;

wherein:

the first nucleic acid and the second nucleic acid are present on the same or different vectors;

the guide RNA includes a direct repeat sequence and a targeting sequence from the 5' to 3', and the targeting sequence can hybridize with the target sequence;

the guide RNA can form a complex with the effector protein or fusion protein as described in (i).

In certain embodiments, the direct repeat sequence is an isolated nucleic acid molecule as defined in the fourth aspect.

In certain embodiments, the targeting sequence is connected to the 3' end of the direct repeat sequence. In certain embodiments, the targeting sequence comprises the complementary sequence of the target sequence.

In certain embodiments, the composition does not include tracrRNA.

In certain embodiments, the composition is non-naturally occurring or modified. In certain embodiments, at least one component of the composition is non-naturally occurring or modified.

In certain embodiments, the first regulatory element is a promoter, such as an inducible promoter.

In certain embodiments, the second regulatory element is a promoter, such as an inducible promoter.

In certain embodiments, when the target sequence is DNA, the target sequence is located at the 3' end of the protospacer adjacent motif (PAM), and the PAM has a sequence shown by 5'-TTN, wherein N is selected from A, G, T, C. In certain embodiments, N is selected from A, T, and C.

In certain embodiments, when the target sequence is RNA, the target sequence does not have PAM domain restrictions.

In certain embodiments, the target sequence is a DNA or RNA sequence derived from a prokaryotic cell or a eukaryotic cell. In certain embodiments, the target sequence is a non-naturally occurring DNA or RNA sequence.

In certain embodiments, the target sequence is present in the cell. In certain embodiments, the target sequence is present in the cell nucleus or in the cytoplasm (such as, organelles). In certain embodiments, the cell is a eukaryotic cell. In certain embodiments, the cell is a prokaryotic cell.

In certain embodiments, the protein is linked to one or more NLS sequences. In certain embodiments, the conjugate or fusion protein comprises one or more NLS sequences. In certain embodiments, the NLS sequence is linked to the N-terminus or C-terminus of the protein. In certain embodiments, the NLS sequence is fused to the N-terminus or C-terminus of the protein.

In certain embodiments, one type of vector is a plasmid, which refers to a circular double-stranded DNA loop into which additional DNA fragments can be inserted, for example, by standard molecular cloning techniques. Another type of vector is a viral vector, in which virus-derived DNA or RNA sequences are present in the vector used to package the virus (for example, retrovirus, replication-defective retrovirus, adenovirus, replication-defective adenovirus, and adeno-associated virus). Viral vectors also contain polynucleotides carried by the virus used for transfection into a host cell. Certain vectors (for example, bacterial vectors with a bacterial origin of replication and episomal mammalian vectors) are capable of autonomous replication in the host cell into which they are introduced. Other vectors (e.g., non-episomal mammalian vectors) are integrated into the host cell's genome after being introduced into the host cell, and thus replicate with the host genome. Moreover, certain vectors can direct the expression of genes to which they are operationally linked. Such vectors are referred to herein as "expression vectors". Common expression vectors used in recombinant DNA technology are usually in the form of plasmids.

Recombinant expression vectors may contain the nucleic acid molecule of the present invention in a form suitable for expression of the nucleic acid in a host cell, which means that these recombinant expression vectors contain one or more regulatory elements selected based on the host cell to be used for expression. The regulatory element is operationally linked to the nucleic acid sequence to be expressed.

Delivery and Delivery Composition

The protein, conjugate, fusion protein of the present invention, the isolated nucleic acid molecule as described in the fourth aspect, the complex of the present invention, the isolated nucleic acid molecule as described in the sixth aspect, the vector as described in the seventh aspect, the composition as described in the ninth and tenth aspects can be delivered by any method known in the art. Such methods include, but are not limited to, electroporation, lipofection, nuclear transfection, microinjection, sonoporation, gene gun, calcium phosphate-mediated transfection, cationic transfection, liposome transfection, dendritic transfection, heat shock transfection, nuclear transfection, magnetic transfection, lipofection, puncture transfection, optical transfection, reagent-enhanced nucleic acid uptake, and delivery via liposome, immunoliposome, viral particle, artificial virosome etc.

Therefore, in another aspect, the present invention provides a delivery composition comprising a delivery vehicle and one or more selected from the following: the protein, conjugate, fusion protein of the present invention, the isolated nucleic acid molecule according to the fourth aspect, the complex of the present invention, the isolated nucleic acid molecule according to the sixth aspect, the vector according to the seventh aspect, the composition according to the ninth and tenth aspects.

In certain embodiments, the delivery vehicle is a particle.

In certain embodiments, the delivery vehicle is selected from a lipid particle, sugar particle, metal particle, protein particle, liposome, exosome, microvesicle, gene gun, or viral vector (e.g., replication defective retrovirus, lentivirus, adenovirus or adeno-associated virus).

Kit

In another aspect, the present invention provides a kit comprising one or more of the components as described above. In certain embodiments, the kit includes one or more components selected from the following: the protein, conjugate, fusion protein of the present invention, the isolated nucleic acid molecule as described in the fourth aspect, the complex of the present invention, the isolated nucleic acid molecule as described in the sixth aspect, the vector as described in the seventh aspect, and the composition as described in the ninth and tenth aspects.

In certain embodiments, the kit of the present invention comprises the composition as described in the ninth aspect. In certain embodiments, the kit further includes instructions for using the composition.

In certain embodiments, the kit of the present invention comprises a composition as described in the tenth aspect. In certain embodiments, the kit further includes instructions for using the composition.

In certain embodiments, the component contained in the kit of the present invention may be provided in any suitable container.

In certain embodiments, the kit further includes one or more buffers. The buffer can be any buffer, including but not limited to sodium carbonate buffer, sodium bicarbonate buffer, borate buffer, Tris buffer, MOPS buffer, HEPES buffer, and combinations thereof. In certain embodiments, the buffer is alkaline. In certain embodiments, the buffer has a pH of from about 7 to about 10.

In certain embodiments, the kit further includes one or more oligonucleotides corresponding to a targeting sequence for insertion into the vector so as to link the targeting sequence and regulatory element operationally. In certain embodiments, the kit includes a homologous recombination template polynucleotide.

Method and Use

In another aspect, the present invention provides a method for modifying a target gene, which comprises: contacting the complex according to the fifth aspect, the composition according to the ninth aspect, or the composition according to the tenth aspect with the target gene, or delivering that to a cell containing the target gene; the target sequence is present in the target gene.

In certain embodiments, the target gene is present in the cell. In certain embodiments, the cell is a prokaryotic cell. In certain embodiments, the cell is a eukaryotic cell. In certain embodiments, the cell is a mammalian cell. In certain embodiments, the cell is a human cell. In certain embodiments, the cell is selected from a non-human primate, bovine, pig, or rodent cell. In certain embodiments, the cell is a non-mammalian eukaryotic cell, such as poultry or fish and the like. In certain embodiments, the cell is a plant cell, such as a cell possessed by a cultivated plant (such as cassava, corn, sorghum, wheat, or rice), algae, tree, or vegetable.

In certain embodiments, the target gene is present in a nucleic acid molecule (e.g., a plasmid) in vitro. In certain embodiments, the target gene is present in a plasmid.

In certain embodiments, the modification refers to a break in the target sequence, such as a double-strand break in DNA or a single-strand break in RNA.

In certain embodiments, the break results in decreased transcription of the target gene.

In certain embodiments, the method further comprises: contacting the editing template with the target gene, or delivering it to the cell containing the target gene. In such embodiments, the method repairs the broken target gene by homologous recombination with an exogenous template polynucleotide, wherein the repair results in a mutation including the insertion, deletion, or substitution of one or more nucleotides of the target gene. In certain embodiments, the mutation results in one or more amino acid changes in the protein expressed from the gene containing the target sequence.

Therefore, in certain embodiments, the modification further includes inserting an editing template (for example, an exogenous nucleic acid) into the break.

In certain embodiments, the protein, conjugate, fusion protein, isolated nucleic acid molecule, complex, vector or composition is contained in a delivery vehicle.

In certain embodiments, the delivery vehicle is selected from a lipid particle, sugar particle, metal particle, protein particle, liposome, exosome, viral vector (such as replication-defective retrovirus, lentivirus, adenovirus or adeno-associated virus).

In certain embodiments, the method is used to change one or more target sequences in a target gene or a nucleic acid molecule encoding a target gene product to modify a cell, cell line, or organism.

In another aspect, the present invention provides a method for altering the expression of a gene product, which comprises: contacting the complex according to the fifth aspect, the composition according to the ninth aspect or the composition according to the tenth aspect with a nucleic acid molecule encoding the gene product, or delivering that to a cell containing the nucleic acid molecule in which the target sequence is present.

In certain embodiments, the nucleic acid molecule is present in a cell. In certain embodiments, the cell is a prokaryotic cell. In certain embodiments, the cell is a eukaryotic cell. In certain embodiments, the cell is a mammalian cell. In certain embodiments, the cell is a human cell. In certain embodiments, the cell is selected from a non-human primate, bovine, pig, or rodent cell. In certain embodiments, the cell is a non-mammalian eukaryotic cell, such as poultry or fish and the like. In certain embodiments, the cell is a plant cell, such as a cell possessed by a cultivated plant (such as cassava, corn, sorghum, wheat, or rice), algae, tree, or vegetable.

In certain embodiments, the nucleic acid molecule is present in a nucleic acid molecule (e.g., a plasmid) in vitro. In certain embodiments, the nucleic acid molecule is present in a plasmid.

In certain embodiments, the expression of the gene product is altered (e.g., enhanced or decreased). In certain embodiments, the expression of the gene product is enhanced. In certain embodiments, the expression of the gene product is reduced.

In certain embodiments, the gene product is a protein.

In certain embodiments, the protein, conjugate, fusion protein, isolated nucleic acid molecule, complex, vector or composition is contained in a delivery vehicle.

In certain embodiments, the delivery vehicle is selected from a lipid particle, sugar particle, metal particle, protein particle, liposome, exosome, viral vector (such as replication-defective retrovirus, lentivirus, adenovirus or adeno-associated virus).

In certain embodiments, the method is used to change one or more target sequences in a target gene or a nucleic acid molecule encoding a target gene product to modify a cell, cell line, or organism.

In another aspect, the present invention relates to a use of the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention for the nucleic acid editing.

In certain embodiments, the nucleic acid editing includes gene or genome editing, such as modifying genes, knocking out genes, altering the expression of gene products, repairing mutations, and/or inserting polynucleotides.

In another aspect, the present invention relates to a use of the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention in the preparation of a formulation, which is used for:

(i) the isolated gene or genome editing;

(ii) the detection of an isolated single-stranded DNA;

(iii) editing the target sequence in the target locus to modify a organism or non-human organism;

(iv) treating the disease caused by defects in the target sequence in the target locus.

Cells and Cell Progeny

In some cases, the modifications introduced into the cell by the method of the present invention can cause the cell and its progeny to be altered to improve the production of its biological products (such as antibodies, starch, ethanol, or other desired cell output). In some cases, the modifications introduced into the cell by the methods of the present invention can cause the cell and its progeny to include changes that alter the biological product produced.

Therefore, in another aspect, the present invention also relates to a cell or its progeny obtained by the method as described above, wherein the cell contains a modification that is not present in its wild type.

The present invention also relates to the cell product of the cell or its progeny as described above.

The present invention also relates to an in vitro, isolated or in vivo cell or cell line or their progeny, the cell or cell line or their progeny comprises: the protein according to the first aspect, the conjugate according to the second aspect, the fusion protein according to the third aspect, the isolated nucleic acid molecule according to the fourth aspect, the complex according to the fifth aspect, the isolated nucleic acid molecule according to the sixth aspect, the vector according to the seventh aspect, the composition according to the ninth aspect, the composition according to the tenth aspect of the present invention, the kit or delivery composition of the present invention.

In certain embodiments, the cell is a prokaryotic cell.

In certain embodiments, the cell is an eukaryotic cell. In certain embodiments, the cell is a mammalian cell. In certain embodiments, the cell is a human cell. In certain embodiments, the cell is a non-human mammalian cell, such as a cell of a non-human primate, cow, sheep, pig, dog, monkey, rabbit, rodent (e.g., rat or mouse). In certain embodiments, the cell is a non-mammalian eukaryotic cell, such as a poultry bird (e.g., chicken), fish, or crustacean (e.g., clam, shrimp) cell. In certain embodiments, the cell is a plant cell, such as a cell possessed by a monocotyledon or dicotyledon or a cell possessed by a cultivated plant or a food crop such as cassava, corn, sorghum, soybean, wheat, oats or rice, such as algae, trees or production plants, fruits or vegetables (for example, trees such as citrus trees, nut trees; nightshades, cotton, tobacco, tomatoes, grapes, coffee, cocoa, etc.).

In certain embodiments, the cell is a stem cell or stem cell line.

Definition of Terms

In the present invention, unless otherwise specified, the scientific and technical terms used herein have the meanings commonly understood by those skilled in the art. In addition, the molecular genetics, nucleic acid chemistry, chemistry, molecular biology, biochemistry, cell culture, microbiology, cell biology, genomics and recombinant DNA and other procedures used in this article are all routine procedures widely used in the corresponding fields. At the same time, in order to better understand the present invention, definitions and explanations of related terms are provided below.

In the present invention, the expression "Cas12f" refers to a Cas effector protein discovered and identified for the first time by the present inventors, which has an amino acid sequence selected from the following:

(i) a sequence as shown in any one of SEQ ID NOs: 1, 2, 3;

(ii) compared with the sequence as shown in any one of SEQ ID NOs: 1, 2, 3, a sequence having one or more amino acid substitutions, deletions or additions (for example, 1, 2, 3, 4, 5, 6, 7, 8, 9 or 10 amino acid substitutions, deletions or additions); or (iii) a sequence having at least 20%, at least 30%, at least 40%, at least 50%, at least 60%, at least 70%, at least 80%, at least 80%, at least 85%, at least 90%, at least 91%, at least 92%, at least 93%, at least 94%, at least 95%, at least 96%, at least 97%, at least 98%, or at least 99% sequence identity with the sequence as shown in any one of SEQ ID NOs: 1, 2, 3.

The Cas12f of the present invention is an endonuclease that binds to and cleaves a specific site of a target sequence under the guidance of a guide RNA, and has DNA and RNA endonuclease activities at the same time.

As used herein, the terms "Clustered Regularly Interspaced Short Palindromic Repeats (CRISPR)-CRISPR-associated (Cas) (CRISPR-Cas) system" or "CRISPR system" are used interchangeably and have the meaning commonly understood by those skilled in the art, it usually contains transcription products or other elements related to the expression of CRISPR-associated ("Cas") genes, or transcription products or other elements capable of directing the activity of the Cas gene. Such transcription products or other elements may include sequences encoding Cas effector proteins and guide RNAs including CRISPR RNA (crRNA), as well as trans-activating crRNA (tracrRNA) sequences contained in the CRISPR-Cas9 system, or other sequences or transcription products from the CRISPR locus. In the Cas12f-based CRISPR system of the present invention, the tracrRNA sequence is not required.

As used herein, the terms "Cas effector protein" and "Cas effector enzyme" are used interchangeably and refer to any protein present in the CRISPR-Cas system that is greater than 900 amino acids in length. In some cases, this type of protein refers to a protein identified from the Cas locus.

As used herein, the terms "guide RNA" and "mature crRNA" can be used interchangeably and have meanings commonly understood by those skilled in the art. Generally speaking, a guide RNA can contain a direct repeat and a guide sequence, or it essentially consists of or consists of a direct repeat sequence and a targeting sequence (also called a spacer in the context of an endogenous CRISPR system). In some cases, the targeting sequence is any polynucleotide sequence that has sufficient complementarity with the target sequence to hybridize to the target sequence and guide the specific binding of the CRISPR/Cas complex to the target sequence. In certain embodiments, when optimally aligned, the degree of complementarity between the targeting sequence and its corresponding target sequence is at least 50%, at least 60%, at least 70%, at least 80%, at least 90%, at least 95%, or at least 99%. Determining the best alignment is within the ability of a person of ordinary skill in the art. For example, there are published and commercially available alignment algorithms and programs, such as but not limited to ClustalW, Smith-Waterman algorithm in matlab, Bowtie, Geneious, Biopython, and SeqMan.

In some cases, the targeting sequence is at least 5, at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 nucleotides in length. In some cases, the targeting sequence is no more than 50, 45, 40, 35, 30, 25, 24, 23, 22, 21, 20, 15, 10 or fewer nucleotides in length. In certain embodiments, the targeting sequence is 10-30, or 15-25, or 15-22, or 19-25, or 19-22 nucleotides in length.

In some cases, the direct repeat sequence is at least 10, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 56, at least 57, at least 58, at least 59, at least 60, at least 61, at least 62, at least 63, at least 64, at least 65, or at least 70 nucleotides in length. In some cases, the direct repeat sequence is no more than 70, 65, 64, 63, 62, 61, 60, 59, 58, 57, 56, 55, 50, 45, 40, 35, 30, 29, 28, 27, 26, 25, 24, 23, 22, 21, 20, 15, 10 or fewer nucleotides in length. In certain embodiments, the direct repeat sequence is 55-70 nucleotides in length, such as 55-65 nucleotides, such as 60-65 nucleotides, such as 62-65 nucleotides, such as 63-64 nucleotides. In certain embodiments, the direct repeat sequence is 15-30 nucleotides in length, such as 15-25 nucleotides, such as 20-25 nucleotides, such as 22-24 nucleosides, such as 23 nucleotides.

As used herein, the term "CRISPR/Cas complex" refers to a ribonucleoprotein complex formed by the combination of guide RNA or mature crRNA and Cas protein, which contains a targeting sequence that hybridizes to the target sequence and binds to the Cas protein. The ribonucleoprotein complex can recognize and cleave polynucleotides that can hybridize with the guide RNA or mature crRNA.

Therefore, in the case of forming a CRISPR/Cas complex, the "target sequence" refers to a polynucleotide that is targeted by a targeting sequence designed to have targeting, for example, a sequence that is complementary to the targeting sequence, wherein the hybridization between the target sequence and the targeting sequence will promote the formation of the CRISPR/Cas complex. Complete complementarity is not necessary, as long as there is sufficient complementarity to cause hybridization and promote the formation of a CRISPR/Cas complex. The target sequence can comprise any polynucleotide, such as DNA or RNA. In some cases, the target sequence is located in the nucleus or cytoplasm of the cell. In some cases, the target sequence may be located in an organelle of an eukaryotic cell such as mitochondria or chloroplast. The sequence or template that can be used to be recombined into the target locus containing the target sequence is referred to as "editing template" or "editing polynucleotide" or "editing sequence". In certain embodiments, the editing template is an exogenous nucleic acid. In certain embodiments, the recombination is a homologous recombination.

In the present invention, the expression "target sequence" or "target polynucleotide" can be any endogenous or exogenous polynucleotide for a cell (for example, a eukaryotic cell). For example, the target polynucleotide may be a polynucleotide present in the nucleus of a eukaryotic cell. The target polynucleotide may be a sequence encoding a gene product (e.g., protein) or a non-coding sequence (e.g., regulatory polynucleotide or useless DNA). In some cases, it is believed that the target sequence should be related to the protospacer adjacent motif (PAM). The exact sequence and length requirements for PAM vary depending on the Cas effector enzyme used, but PAM is typically a 2-5 base pair sequence adjacent to the protospacer (i.e., the target sequence). Those skilled in the art are able to identify the PAM sequence to be used with a given Cas effector protein.

In some cases, the target sequence or target polynucleotide may include multiple disease-related genes and polynucleotides and signal transduction biochemical pathway-related genes and polynucleotides. Non-limiting examples of such target sequences or target polynucleotides include those listed in U.S. Provisional Patent Applications 61/736,527 and 61/748,427 filed on Dec. 12, 2012 and Jan. 2, 2013, respectively, and the international application PCT/US2013/074667 filed on Dec. 12, 2013, which are all incorporated herein by reference.

In some cases, examples of a target sequence or a target polynucleotide includes a sequence related to signaling biochemical pathways, such as a signaling biochemical pathway related gene or polynucleotide. Examples of a target polynucleotide includes a disease-related gene or polynucleotide. The "disease-related" gene or polynucleotide refers to any gene or polynucleotide that produces transcription or translation products at abnormal levels or in abnormal forms in cells derived from tissues affected by the disease, compared with non-disease control tissues or cells. In the case where the altered expression is related to the appearance and/or progression of the disease, it may be a
gene expressed at an abnormally high level; or, it may be a
gene expressed at an abnormally low level. The disease-
related gene also refers to genes that have one or more
mutations or genetic variations that are directly responsible
for or genetic linkage disequilibrium with one or more genes
responsible for the etiology of the disease. The transcribed
or translated product can be known or unknown, and can be
at normal or abnormal levels.

As used herein, the term "wild-type" has the meaning
commonly understood by those skilled in the art, which
means a typical form of organisms, strains, genes, or fea-
tures that distinguish it from mutants or variant forms when
it exists in nature, it can be isolated from natural sources and
has not been deliberately modified.

As used herein, the terms "non-naturally occurring" or
"engineered" can be used interchangeably and refer to
artificial involvement. When these terms are used to describe
a nucleic acid molecule or polypeptide, it means that the
nucleic acid molecule or polypeptide is at least substantially
free from at least another component that they bind to in
nature or as found in nature.

As used herein, the term "orthologue (ortholog)" has the
meaning commonly understood by those skilled in the art.
As a further guidance, the "orthologue" of the protein as
described herein refers to proteins belonging to different
species, which perform the same or similar functions as the
proteins that act as their orthologs.

As used herein, the term "identity" is used to refer to the
matching of sequences between two polypeptides or
between two nucleic acids. When a certain position in the
two sequences to be compared is occupied by the same base
or amino acid monomer subunit (for example, a certain
position in each of the two DNA molecules is occupied by
adenine, or a certain position in each of the two peptides is
occupied by lysine), then the molecules are identical at that
position. The "percent identity" between two sequences is a
function of the number of matching positions shared by the
two sequences divided by the number of positions to be
compared×100. For example, if 6 out of 10 positions in two
sequences match, then the two sequences have 60% identity.
For example, the DNA sequences CTGACT and CAGGTT
share 50% identity (3 out of 6 total positions match).
Generally, the comparison is made when two sequences are
aligned to produce maximum identity. Such alignment can
be achieved by using, for example, the method of Needle-
man et al. (1970) J. Mol. Biol. 48:443-453, which can be
conveniently performed by a computer program such as the
Align program (DNAstar, Inc.). It is also possible to use the
algorithm of E. Meyers and W. Miller (Comput. Appl
Biosci., 4:11-17 (1988)) integrated into the ALIGN program
(version 2.0), using the PAM120 weight residue table, a gap
length penalty of 12, and a gap penalty of 4 to determine the
percent identity between two amino acid sequences. In
addition, the Needleman and Wunsch (J Mol Biol. 48:444-
453 (1970)) algorithm in the GAP program integrated into
the GCG software package (available on www.gcg.com) can
be used, the Blossum 62 matrix or PAM250 matrix and gap
weights of 16, 14, 12, 10, 8, 6, or 4 and length weights of 1,
2, 3, 4, 5 or 6 to determine the percent identity between two amino acid sequences.

As used herein, the term "vector" refers to a nucleic acid
delivery vehicle into which a polynucleotide can be inserted.
When the vector can express the protein encoded by the
inserted polynucleotide, the vector is called an expression
vector. The vector can be introduced into the host cell
through transformation, transduction or transfection, so that the genetic material elements which it carries can be
expressed in the host cell. Vector is well-known to those
skilled in the art, including but not limited to: a plasmid;
phagemid; cosmid; artificial chromosome, such as yeast
artificial chromosome (YAC), bacterial artificial chromo-
some (BAC) or P1 derived artificial chromosome (PAC);
bacteriophage such as a lambda bacteriophage or M13
bacteriophage and animal virus. An animal virus that can be
used as a vector includes, but is not limited to, a retrovirus
(including a lentivirus), adenovirus, adeno-associated virus,
herpes virus (such as herpes simplex virus), poxvirus, bacu-
lovirus, papilloma virus, and papovaviruses (such as SV40).
A vector can contain a variety of elements that control
expression, including but not limited to a promoter
sequence, transcription initiation sequence, enhancer
sequence, selection element, and reporter gene. In addition,
the vector may also contain an origin of replication.

As used herein, the term "host cell" refers to a cell that can
be used to introduce a vector, which includes, but is not
limited to, a prokaryotic cell such as *Escherichia coli* or
*Bacillus subtilis* and the like, a fungal cell such as a yeast
cell or *Aspergillus*, etc., an insect cell such as a S2 *Droso-
phila* cell or Sf9, etc., or an animal cell such as a fibroblast,
CHO cell, COS cell, NSO cell, HeLa cell, BHK cell, HEK
293 cell or human cell, etc.

Those skilled in the art will understand that the design of
the expression vector may depend on factors such as the
selection of the host cell to be transformed, the desired
expression level, and the like. A vector can be introduced
into a host cell to thereby produce transcripts, proteins, or
peptides, including proteins, fusion proteins, isolated nucleic
acid molecules, etc. as described herein (for example,
CRISPR transcripts, such as nucleic acid transcripts, pro-
teins, or enzymes).

As used herein, the term "regulatory element" is intended
to include a promoter, enhancer, internal ribosome entry site
(IRES), and other expression control elements (e.g., tran-
scription termination signals, such as polyadenylation sig-
nals and Poly U sequence), for a detailed description, please
refer to Goeddel, "GENE EXPRESSION TECHNOLOGY:
METHOD IN ENZYMOLOGY" 185, Academic Press, San
Diego, California (1990). In some cases, the regulatory
element includes those that direct the constitutive expression
of a nucleotide sequence in many types of host cells and
those that direct the expression of the nucleotide sequence
only in certain host cells (for example, tissue-specific regu-
latory sequence). An tissue-specific promoter may mainly
direct expression in desired tissues of interest, such as
muscles, neurons, bone, skin, blood, specific organs (such as
liver, pancreas), or specific cell types (such as lymphocytes).
In some cases, the regulatory element may also direct
expression in a time-dependent manner (such as in a cell
cycle-dependent or developmental stage-dependent man-
ner), which may be or may not be tissue or cell type specific.
In some cases, the term "regulatory element" encompasses
an enhancer element, such as WPRE; a CMV enhancer;
R-U5' fragment in the LTR of HTLV-I ((Mol. Cell. Biol.,
Volume 8(1), Pages 466-472, 1988); SV40 enhancer; and the
intron sequence between exons 2 and 3 of rabbit β-globin
(Proc. Natl. Acad. Sci. USA., Vol. 78(3), pp. 1527-31, 1981).

As used herein, the term "promoter" has the meaning well
known to those skilled in the art, which refers to a non-
coding nucleotide sequence located upstream of a gene and
capable of promoting downstream gene expression. A con-
stitutive promoter is such a nucleotide sequence: when it is
operationally linked to a polynucleotide encoding or defin-
ing a gene product, it leads to the production of a gene product in the cell under most or all physiological conditions of the cell. An inducible promoter is such a nucleotide sequence that, when operationally linked to a polynucleotide encoding or defining a gene product, basically only when an inducer corresponding to the promoter is present in the cell, it leads to the gene product to be produced in the cell. A tissue-specific promoter is such a nucleotide sequence that, when operationally linked to a polynucleotide encoding or defining a gene product, basically only when the cell is a cell of the tissue type corresponding to the promoter, it leads to the production of gene products in the cell.

As used herein, the term "operationally linked" is intended to mean that the nucleotide sequence of interest is linked to the one or more regulatory elements in a manner that allows the expression of the nucleotide sequence (e.g., in an in vitro transcription/translation system or when the vector is introduced into the host cell, it is in the host cell).

As used herein, the term "complementarity" refers to the ability of a nucleic acid to form one or more hydrogen bonds with another nucleic acid sequence by means of traditional Watson-Crick or other non-traditional types. The percentage of complementarity represents the percentage of residues in a nucleic acid molecule that can form hydrogen bonds (e.g., Watson-Crick base pairing) with a second nucleic acid sequence (e.g., 5, 6, 7, 8, 9, 10 out of 10 are 50%, 60%, 70%, 80%, 90%, and 100% complementary). "Completely complementary" means that all consecutive residues of a nucleic acid sequence form hydrogen bonds with the same number of consecutive residues in a second nucleic acid sequence. As used herein, "substantially complementary" means that there are at least 60%, 65%, 70%, 75%, 80%, 85%, 90%, 95%, 97%, 98%, 99%, or 100% degree of complementarity in a region of 8, 9, 10, 11, 12, 13, 14, 15, 16, 17, 18, 19, 20, 21, 22, 23, 24, 25, 30, 35, 40, 45, 50 or more nucleotides, or refers to two nucleic acids that hybridize under stringent conditions.

As used herein, "stringent conditions" for hybridization refer to conditions under which a nucleic acid having complementarity with a target sequence mainly hybridizes to the target sequence and substantially does not hybridize to a non-target sequence. Stringent conditions are usually sequence-dependent and vary depending on many factors. Generally speaking, the longer the sequence, the higher the temperature at which the sequence specifically hybridizes to its target sequence. Non-limiting examples of stringent conditions are described in "Laboratory Techniques In Biochemistry And Molecular Biology-Hybridization With Nucleic Acid Probes" by Tijssen (1993), Part I, Chapter 2, "Overview of principles of hybridization and the strategy of nucleic acid probe assay", Elsevier, New York.

As used herein, the term "hybridization" refers to a reaction in which one or more polynucleotides react to form a complex that is stabilized by hydrogen bonding of bases between these nucleotide residues. Hydrogen bonding can occur by means of Watson-Crick base pairing, Hoogstein binding, or in any other sequence-specific manner. The complex may comprise two strands forming a duplex, three or more strands forming a multi-strand complex, a single self-hybridizing strand, or any combination of these. The hybridization reaction can constitute a step in a broader process (such as the beginning of PCR, or the cleavage of polynucleotides by an enzyme). A sequence that can hybridize to a given sequence is called the "complement" of the given sequence.

As used herein, the term "expression" refers to the process by which the DNA template is transcribed into polynucleotides (such as mRNA or other RNA transcripts) and/or the process by which the transcribed mRNA is subsequently translated into peptides, polypeptides or proteins. The transcript and the encoded polypeptide can be collectively referred to as a "gene product". If the polynucleotide is derived from a genomic DNA, the expression can include splicing of mRNA in eukaryotic cells.

As used herein, the term "linker" refers to a linear polypeptide formed by multiple amino acid residues connected by peptide bonds. The linker of the present invention may be an artificially synthesized amino acid sequence, or a naturally-occurring polypeptide sequence, such as a polypeptide having the function of a hinge region. Such linker polypeptides are well known in the art (see, for example, Holliger, P. et al. (1993) Proc. Natl. Acad. Sci. USA 90: 6444-6448; Poljak, R J et al. (1994) Structure 2: 1121-1123).

As used herein, the term "treatment" refers to treating or curing a disorder, delaying the onset of symptoms of the disorder, and/or delaying the development of the disorder.

As used herein, the term "subject" includes, but is not limited to, various animals, such as mammals, e.g., bovines, equines, caprids, swines, canines, felines, leporidae animals, rodents (for example, mice or rats), non-human primates (for example, macaques or cynomolgus), or humans. In certain embodiments, the subject (e.g., human) has a disorder (e.g., a disorder caused by a disease-related gene defect).

The Beneficial Effects of the Present Invention

Compared with the prior art, the Cas protein and system of the present invention have significant advantages. For example, the PAM domain of the Cas effector protein of the present invention is a strict 5'-TTN structure, and nearly 100% of the second and third bases in front of the target sequence are T, and the other positions can be arbitrary sequences. It has a more rigorous PAM recognition method than the most rigorous PAM recognition C2c1 that has been reported so far, which significantly reduces off-target effects. For example, the Cas effector protein of the present invention can perform DNA cleavage in eukaryotes, and its molecular size is about 200-300 amino acids smaller than Cpf1 and Cas9 proteins, so that the transfection efficiency is significantly better than Cpf1 and Cas9.

The embodiments of the present invention will be described in detail below in conjunction with the accompanying drawings and examples. However, those skilled in the art will understand that the following drawings and examples are only used to illustrate the present invention, but not to limit the scope of the present invention. According to the accompanying drawings and the following detailed description of the preferred embodiments, various objects and advantageous aspects of the present invention will become apparent to those skilled in the art.

DESCRIPTION OF THE DRAWINGS

FIG. 3a-FIG. 3c are the results of the detection of the cleavage activity of Cas12f.4 in a human cell line in Example 4.

FIG. 4a-FIG. 4c are the results of the detection of the cleavage activity of Cas12f.4 in a maize protoplast cell in Example 5.

SEQUENCE INFORMATION

Figure 1:
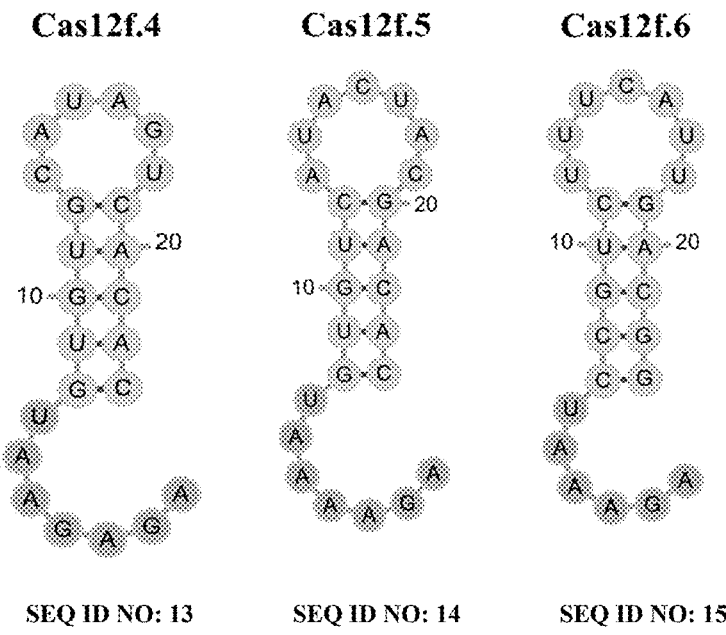
FIG. 1 is the result of the crRNA structure analysis of Cas12f.4, Cas12f.5 and Cas12f.6 in Example 2, showing the secondary structure of the Repeat sequence.

Information on partial sequences involved in the present invention is provided in Table 1 below.

TABLE 1

Description of the sequence

| SEQ ID NO: | Description |
|---|---|
| 1 | an amino acid sequence of Cas12f.4 |
| 2 | an amino acid sequence of Cas12f.5 |
| 3 | an amino acid sequence of Cas12f.6 |
| 4 | a coding nucleic acid sequence of Cas12f.4 |
| 5 | a coding nucleic acid sequence of Cas12f.5 |
| 6 | a coding nucleic acid sequence of Cas12f.6 |
| 7 | Cas12f.4/prototype direct repeat |
| 8 | Cas12f.5/prototype direct repeat |
| 9 | Cas12f.6/prototype direct repeat |
| 10 | Cas12f.4/a coding nucleic acid sequence of prototype direct repeat |
| 11 | Cas12f.5/a coding nucleic acid sequence of prototype direct repeat |
| 12 | Cas12f.6/a coding nucleic acid sequence of prototype direct repeat |
| 13 | Cas12f.4/mature direct repeat |
| 14 | Cas12f.5/mature direct repeat |
| 15 | Cas12f.6/mature direct repeat |
| 16 | Cas12f.4/a coding nucleic acid sequence of mature direct repeat |
| 17 | Cas12f.5/a coding nucleic acid sequence of mature direct repeat |
| 18 | Cas12f.6/a coding nucleic acid sequence of mature direct repeat |
| 19 | NLS sequence |
| 20 | an amino acid sequence of Cas12f.4-NLS fusion protein |
| 21 | an amino acid sequence of Cas12f.5-NLS fusion protein |
| 22 | an amino acid sequence of Cas12f.6-NLS fusion protein |
| 23 | a plasmid expressing Cas12f.4 system |
| 24 | PAM library sequence |
| 25 | guide RNA-VEGFA of Cas12f.4 system |
| 26 | guide RNA-VEGFA of Cas12f.5 system |
| 27 | guide RNA-VEGFA of Cas12f.6 system |
| 28 | guide RNA-PDI1 of Cas12f.4 system |
| 29 | guide RNA-SBE2.2 of Cas12f.4 system |

DETAILED DESCRIPTION

The invention will now be described with reference to the following examples which are intended to illustrate the present invention rather than limit the present invention.

Unless otherwise specified, the experiments and methods described in the examples are basically performed according to conventional methods well known in the art and described in various references. For example, conventional techniques such as immunology, biochemistry, chemistry, molecular biology, microbiology, cell biology, genomics, and recombinant DNA used in the present invention can be found in Sambrook, Fritsch and Maniatis, "MOLECULAR CLONING: A LABORATORY MANUAL", 2nd edition (1989); "CURRENT PROTOCOLS IN MOLECULAR BIOLOGY" (edited by F. M. Ausubel et al., (1987)); "METHODS IN ENZYMOLOGY" series (Academic Publishing Company): "PCR 2: A PRACTICAL APPROACH" (edited by M. J. MacPherson, B D Hames and G. R. Taylor (1995)), "ANTI-BODIES, A LABORATORY MANUAL", edited by Harlow and Lane (1988), and "ANIMAL CELL CULTURE" (edited by R. I. Freshney (1987)).

In addition, if the specific conditions are not specified in the examples, it shall be carried out in accordance with the conventional conditions or the conditions recommended by the manufacturer. The reagents or instruments used without the manufacturer's indication are all conventional products that can be purchased commercially. Those skilled in the art know that the embodiments describe the present invention by way of example, and are not intended to limit the scope of protection claimed by the present invention. All publications and other references mentioned in this article are incorporated into this article by reference in their entirety.

The sources of some reagents involved in the following examples are as follows:

LB liquid medium: 10 g Tryptone, 5 g Yeast Extract, 10 g NaCl, diluted to 1 L, and sterilized. If antibiotics are needed, they are added at a final concentration of 50 μg/ml after cooling the medium.

Chloroform/isoamyl alcohol: adding 240 ml of chloroform to 10 ml of isoamyl alcohol and mixing them well.

RNP buffer: 100 mM sodium chloride, 50 mM Tris-HCl, 10 mM $MgCl_2$, 100 μg/ml BSA, pH 7.9.

The prokaryotic expression vectors pACYC-Duet-1 and pUC19 are purchased from Beijing Quanshijin Biotechnology Co., Ltd.

*E. coli* competence EC100 is purchased from Epicentre company.

Example 1. Acquisition of Cas12f Gene and Cas12f Guide RNA

1. CRISPR and gene annotation: Using Prodigal to perform gene annotation on the microbial genome and metagenomic data of NCBI and JGI databases to obtain all proteins and at the same time, using Piler-CR to annotate CRISPR locus. All parameters are the default parameters.

2. Protein filtering: Eliminating redundancy of annotated proteins by sequence identity, removing proteins with exactly identical sequence, and at the same time classifying proteins longer than 800 amino acids into macromolecular proteins. Since all the effector proteins of the second type of CRISPR/Cas system discovered so far are more than 900 amino acids in length, in order to reduce the computational complexity, when we explore CRISPR effector proteins, we only consider macromolecular proteins.

3. Obtaining CRISPR-associated macromolecular proteins: extending each CRISPR locus by 10 Kb upstream and downstream, and identifying non-redundant macromolecular proteins in the adjacent interval of CRISPR.

4. Clustering of CRISPR-associated macromolecular proteins: using BLASTP to perform internal pairwise comparisons of non-redundant macromolecular CRISPR-associated proteins, and output the comparison result of Evalue<1E-10. Using MCL to perform cluster analysis on the output result of BLASTP, CRISPR-associated protein family.

5. Identification of CRISPR-enriched macromolecular protein family: using BLASTP to compare the proteins of the CRISPR-associated protein family to the non-redundant macromolecular protein database that removes the CRISPR-associated proteins and output the comparison result of Evalue<1E-10. If the homologous protein found in a non-CRISPR-related protein database is less than 100%, it means that the proteins of this family are enriched in the CRISPR region. In this way, we identify the CRISPR-enriched macromolecular protein family.

6. Annotation of protein functions and domains: using the Pfam database, NR database and Cas protein collected from NCBI to annotate the CRISPR-enriched macromolecular protein family to obtain a new CRISPR/Cas protein family. Using Mafft to perform multiple sequence alignments for each CRISPR/Cas family protein, and then using JPred and HHpred to perform conserved domain analysis to identify protein families containing RuvC domains.

On this basis, the present inventors have obtained a new Cas effector protein, namely Cas12f, named Cas12f.4 (SEQ ID NO: 1), Cas12f.5 (SEQ ID NO: 2) and Cas12f.6 (SEQ ID NO: 3), respectively with its three active homologue sequences. the coding DNA of the three homologues are shown in SEQ ID NOs: 4, 5, and 6, respectively. The prototype direct repeat sequences (repeat sequences contained in pre-crRNA) corresponding to Cas12f.4, Cas12f.5, and Cas12f.6 are shown in SEQ ID NOs: 7, 8, and 9, respectively. The mature direct repeat sequences (repeat sequences contained in mature crRNA) corresponding to Cas12f.4, Cas12f.5, and Cas12f.6 are shown in SEQ ID NOs: 13, 14, and 15, respectively.

Example 2. Processing of Mature crRNA by Cas12f Gene

1. The double-stranded DNA molecule as shown in SEQ ID NO: 4 was artificially synthesized, and the double-stranded DNA molecule as shown in SEQ ID NO: 10 was artificially synthesized at the same time.

2. Connecting the double-stranded DNA molecule synthesized in step 1 with the prokaryotic expression vector pACYC-Duet-1 to obtain the recombinant plasmid pACYC-Duet-1+CRISPR/Cas12f.

The recombinant plasmid pACYC-Duet-1+CRISPR/Cas12f was sequenced. Sequencing results show that the recombinant plasmid pACYC-Duet-1+CRISPR/Cas12f contains the sequences as shown in SEQ ID NO: 4 and SEQ ID NO: 10, and expresses the Cas12f.4 protein as shown in SEQ ID NO: 1 and the Cas12f.4 prototype direct repeat sequence as shown in SEQ ID NO: 7. The recombinant plasmid pACYC-Duet-1+CRISPR/Cas12f was introduced into E. coli EC100 to obtain a recombinant bacteria, which was named EC100-CRISPR/Cas12f.

3. Taking a single clone of EC100-CRISPR/Cas12f, inoculating it into 100 mL LB liquid medium (containing 50 μg/mL ampicillin), culturing with shaking at 37° C. and 200 rpm for 12 h to obtain a culture broth.

4. Extracting bacterial RNA: transferring 1.5 mL of bacterial culture to a pre-cooled microcentrifuge tube and centrifuged at 6000×g for 5 minutes at 4° C. After centrifugation, discarding the supernatant, and resuspendings the cell pellet in 2004, Max Bacterial Enhancement Reagent preheated to 95° C. Mixed by pipetting and mixed well, and incubated at 95° C. for 4 minutes. Adding 1 mL of TRIzol® Reagent to the lysate and mixed by pipetting and incubated at room temperature for 5 minutes. Adding 0.2 mL cold chloroform, shaking the tube by hand to mix for 15 seconds, and incubated at room temperature for 2-3 minutes. Centrifuged at 12,000×g for 15 minutes at 4° C. Taking 600 μL of supernatant in a new tube, adding 0.5 mL of cold isopropanol to precipitate RNA, mixed upside down, and incubated at room temperature for 10 minutes. Centrifuged at 15,000×g for 10 minutes at 4° C., discarding the supernatant, adding 1 mL of 75% ethanol, and for the vortex to mix. Centrifuged at 7500×g for 5 minutes at 4° C., discarding the supernatant, and for the air dry. Dissolving the RNA pellet in 504, RNase-free water and incubated at 60° C. for 10 minutes.

5. DNA digestion: 20 ug RNA was dissolved in 39.5 μL, dH₂O, 65° C., 5 min. 5 min on ice, adding 0.5 μL RNAI, 5 μL, buffer, 5 μL, DNaseI, 37° C. for 45 min (50 μL system). Adding 50 μL dH₂O and adjusting the volume to 100 μL. After centrifuging the 2 mL Phase-Lock tube at 16000 g for 30 s, adding 100 μL of phenol:chloroform:isoamyl alcohol (25:24:1), 100 μL of digested RNA, shaked for 15 s, and centrifuged at 16000 g for 12 min at 15° C. Taking the supernatant into a new 1.5 mL centrifuge tube, adding the same volume of isopropanol 1/10 NaoAC as the supernatant, and reacted for 1 hour or −20° C. overnight. Centrifuged at 16000 g for 30 min at 4° C., and discarding the supernatant. Adding 3504, of 75% ethanol to wash the pellet, centrifuged at 16000 g for 10 min at 4° C., and discarding the supernatant. Drying, and adding 20 μL RNase-free water at 65° C. for 5 min to dissolve the precipitate. Using NanoDrop to measure the concentration and running the gel.

6. 3' dephosphorylation and 5' phosphorylation: Adding water to ~20 ug of each digested RNA to 42.5 μL, at 90° C. for 2 min. Cooling on ice for 5 minutes. Adding 54, 10×T4 PNK buffer; 0.5 μL RNaI, 2 μL, T4 PNK (50 μL), at 37° C. for 6 h. Adding 1 μL at T4 PNK, 1.25 μL, (100 mM) ATP, 37° C. for 1 h. Adding 47.75 μL, dH₂O and adjusting the volume to 100 μL. After centrifuging the 2 mL Phase-Lock tube at 16000 g for 30 s, adding 100 μL of phenol:chloroform:isoamyl alcohol (25:24:1), 100 μL of digested RNA, shaking for 15 s, and centrifuged at 16000 g for 12 min at 15° C. Taking the supernatant into a new 1.5 mL centrifuge tube, adding the same volume of isopropanol with the supernatant, the total volume of 1/10 NaoAC, and reacted for 1 hour or −20° C. overnight. Centrifuged at 16000 g for 30 min at 4° C., and discarding the supernatant. Adding 3504, of 75% ethanol to wash the pellet, centrifuged at 16000 g for 10 min at 4° C., and discarding the supernatant. Drying, and adding 21 μL RNase-free water at 65° C. for 5 min to dissolve the precipitate, using NanoDrop to measure the concentration.

7. RNA monophosphorylation: 20 μL RNA, at 90° C. for 1 min, cooling on ice for 5 min. Adding 2 μL RNA 5' Polphosphatase 10×Reaction buffer, 0.5 μL Inhibitor, 1 μL at RNA 5' Polphosphatase (20 Units), and adding RNase-free water to 20 μL, at 37° C. for 60 min. Adding 80 μL dH₂O and adjusting the volume to 100 μL. After centrifuging the 2 mL Phase-Lock tube at 16000 g for 30 s, adding 100 μL of phenol:chloroform:isoamyl alcohol (25:24:1), 100 μL of digested RNA, shaking for 15 s, and centrifuged at 16000 g for 12 min at 15° C. Taking the supernatant in a new 1.5 mL centrifuge tube, adding the same volume of isopropanol with the supernatant, the total volume of 1/10 NaoAC, and reacted for 1 hour or −20° C. overnight. Centrifuged at 16000 g for 30 min at 4° C., discarding the supernatant, adding 3504, of 75% ethanol to wash the precipitate, centrifuged at 16000 g for 10 min at 4° C., discarding the supernatant. Drying, and adding 214, RNase-free water at 65° C. for 5 min to dissolve the precipitate, using NanoDrop to measure the concentration.

8. Preparation of cDNA library: 16.5 μL RNase-free water. 5 μL Poly(A)Polymerase 10×Reaction buffer. 54, 10 mM ATP. 1.5 μL RiboGuard RNase Inhibitor. 204, RNA Substrate. 2 μL Poly(A)Polymerase (4 Units). 504, of total volume at 37° C. for 20 minutes. Adding 504, dH₂O and adjusting the volume to 100 μL. After centrifuging the 2 mL Phase-Lock tube at 16000 g for 30 s, adding 100 μL of phenol:chloroform:isoamyl alcohol (25:24:1), 100 μL of digested RNA, shaking for 15 s, and centrifuged at 16000 g for 12 min. Taking the supernatant into a new 1.5 mL centrifuge tube, adding the same volume of isopropanol with the supernatant, the total volume of 1/10 NaoAC, and reacted for 1 hour or −20° C. overnight. Centrifuged at 16000 g for 30 min at 4° C., discarding the supernatant, drying it, and adding 114, RNase-free water at 65° C. for 5 min to dissolve the precipitate, and measuring the concentration with NanoDrop.

9. Adding the sequencing linker to the cDNA library and sending it to Beijing berrygenomics for sequencing.

10. Performing quality filtering on the original data to remove sequences with an average base quality value lower than 30. After removing the linker from the sequence, the RNA sequence from 25 nt to 50 nt was retained, and aligned to the reference sequence of the CRISPR array with bowtie.

11. Through comparison, we have found that the pre-crRNA of Cas12f.4 can be successfully processed into 45 nt mature crRNA in *E. coli*, which consists of 23 nt Repeat sequence and 19-22 nt targeting sequence. 12. Using ViennaRNA and VARNA to predict and visualize the structure of mature crRNA. We have found that the 3'end of the Repeat sequence of crRNA can form an 8-base neck loop (FIG. 1).

13. After predicting the 23 nt sequence of the 3' end of the crRNA of Cas12f.5 and Cas12f.6, we have found a similar secondary structure (FIG. 1).

Example 3. Identification of the PAM Domain of the Cas12f Gene

1. Constructing the recombinant plasmid pACYC-Duet-1+CRISPR/Cas12f and sequencing it. According to the sequencing results, the structure of the recombinant plasmid pACYC-Duet-1+CRISPR/Cas12f is described as follows: Replacing the small fragment between the recognition sequence of the restriction endonuclease Pml I and Kpn I of the vector pACYC-Duet-1 with the double-stranded sequence shown at positions 1 to 3713 from the 5' end in the sequence as shown in SEQ ID NO: 4. The recombinant plasmid pACYC-Duet-1+CRISPR/Cas12f expresses the Cas12f.4 protein as shown in SEQ ID NO: 1 and the Cas12f guide RNA as shown in SEQ ID NO: 25.

2. The recombinant plasmid pACYC-Duet-1+CRISPR/Cas12f contains an expression cassette, and the nucleotide sequence of the expression cassette is shown in SEQ ID NO: 23. In the sequence as shown in SEQ ID NO: 23, positions 1 to 44 from the 5' end are the nucleotide sequence of the pLacZ promoter, positions 45 to 3326 are the nucleotide sequence of the Cas12f.4 gene, and positions 3327 to 3412 are the nucleotide sequence of the terminator (used to terminate transcription). From the 5' end, positions 3413 to 3452 are the nucleotide sequence of the J23119 promoter, positions 3453 to 3,628 are the nucleotide sequence of the CRISPR array, and positions 3627 to 3713 are the nucleotide sequence of the rrnB-T1 terminator (used to terminate transcription).

3. The acquisition of the recombinant *E. coli*: the recombinant plasmid pACYC-Duet-1+CRISPR/Cas12f was introduced into *E. coli* EC100 to obtain recombinant *E. coli*, named EC100/pACYC-Duet-1+CRISPR/Cas12f. The recombinant plasmid pACYC-Duet-1 was introduced into *E. coli* EC100 to obtain a recombinant *E. coli* named EC100/pACYC-Duet-1.

4. Construction of the PAM library: the sequence shown in SEQ ID NO: 24 is artificially synthesized and connected to the pUC19 vector, wherein the sequence as shown in SEQ ID NO: 24 includes eight random bases at the 5' end and the target sequence. Eight random bases were designed in front of the 5' end of the target sequence of the PAM library to construct a plasmid library. The plasmids were transferred into *Escherichia coli* containing the Cas12f.4 locus and *Escherichia coli* without the Cas.12f.4 locus, respectively. After treatment at 37° C. for 1 hour, we extracted the plasmid, and performed PCR amplification and sequencing on the sequence of the PAM region.

Figure 2:
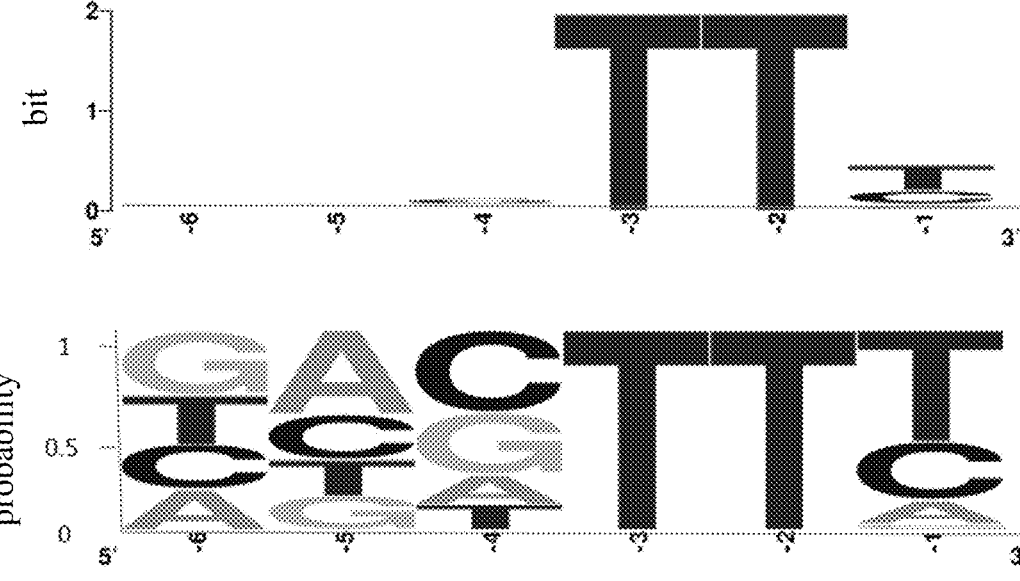
FIG. 2 shows the analysis result of the PAM domain in Example 3.

5. The acquisition of the PAM library domain: the number of occurrences of 65,536 combinations of PAM sequences in the experimental group and the control group were counted, and the number of PAM sequences in each group was used for normalization. For any PAM sequence, when the log 2 (normalized value of the control group/normalized value of the experimental group) is greater than 3.5, we deem that this PAM is significantly consumed. We obtained a total of 3,548 significantly consumed PAM sequences, all accounting for 5.41%. We used Weblogo to predict the significantly consumed PAM sequence and found that the PAM domain of Cas12f.4 was a strict 5'-TTN structure (FIG. 2), and almost 100% of the second and third bases in front of the target sequence were T, and the other positions can be any sequence. This is a more rigorous PAM recognition method than C2c1, which has been reported for the most rigorous PAM recognition.

6. Verification of the PAM library domain: Through the PAM library consumption experiment, we obtained the PAM domain of Cas12f.4. In order to verify the rigor of this domain, we set up 10 groups of PAM for in vivo experiments and sequenced Cas12fs editing activity on these PAMs. First, we integrated the 30 nt target and PAM sequence into the non-conserved position of the Kana gene-resistance of the plasmid, and then mixed it with the complex formed by CRSPR/Cas12f and guide RNA for 8 hours. By coating the plate and counting the number of colonies, we can judge the consumption activity of Cas12f on different PAM sequences. Through the experimental results, we can see that the CRISPR/Cas12f.4 system can only effectively edit the target sequence with 5'-TTA, 5'-TTT, 5'-TTC and 5'-TTG PAM, it has no editing activity on target sequences with 5'-TAT, 5'-TCT, 5'-TCG, 5'-ATT, 5'-CTT and 5'-GTT PAM, thus verifying the verifiability of the PAM domain recognition of Cas12f.4. By counting the colonies of different PAMs, we have found that the editing activity of the CRISPR/Cas12f.4 system on 5'-TTA, 5'-TTT and 5'-TTC is higher than that on 5'-TTG.

Example 4. Cas12f.4, Cas12f.5, Cas12f.6 Cleavage in Human Cell Lines

The eukaryotic expression vector containing the Cas12f.4 gene and the PCR product containing the U6 promoter and crRNA (SEQ ID NO: 25) sequence were transfected into a human HEK293T cell by liposome transfection (FIG. 3a), and incubated for 72 hours at 37 degrees Celsius with 5% carbon dioxide concentration. The DNA of total cells was extracted, and the 700 bp sequence containing the target site was amplified. The PCR products were constructed for next-generation sequencing library through Tn5, and the sequencing was completed by Beijing Annoroad Genomics Technology Co., Ltd. The sequencing results were compared to the VEGFA gene of the human genome, the cleavage method of Cas12f.4 to the target site was identified (FIG. 3b). The editing efficiency of CRISPR/Cas12f.4 system for VEGFA can reach 4.2%. The original sequencing data is shown in FIG. 3c (FIG. 3c).

The same method was used to detect the cleavage activity of Cas12f.5 and Cas12f.6 on VEGFA, and their crRNAs are shown in SEQ ID NO: 26 and SEQ ID NO: 27, respectively. The results in FIG. 3c show that the editing efficiency of CRISPR/Cas12f.5 and CRISPR/Cas12f.6 systems on VEGFA are 0.31% and 0.19%, respectively.

Example 5. Cleavage of Cas12f.4 in a Maize Protoplast

The purified Cas12f.4 protein (60 µg) and the guide RNA (120 µg) as shown in SEQ ID NO: 28 or 29 were mixed at 37 degrees Celsius to form a ribonucleoprotein complex (RNP), and then the CRISPR/Cas12f.4 RNP was transferred into a maize protoplast cell using PEG4000-mediated protoplast transformation, and cultured in the dark at 37 degrees Celsius for 24 hours (FIG. 4a). After the culture, the supernatant was discarded by centrifugation to collect the protoplasts, and the protoplast DNA was extracted. The DNA fragments of about 600 bp upstream and downstream of the target site were amplified. The DNA fragment containing the target site was subjected to T7 endonuclease digestion detection, and the result was shown in FIG. 4b. The CRISPR/Cas12f.4 system has a high-efficiency cleavage activity for PDI1 and SEB2.2. Connecting the DNA fragment containing the target site to the Blunt Simple vector, coating the plate, and using Thermo Fisher Scientific (China) Co., Ltd. to perform Sanger sequencing on the single clone, and comparing the sequencing results to the PDI1 and SEB2.2 genes in the maize group, the results are shown in FIGS. 4b-4c. The cleavage efficiency of Cas12f.4 on the target site is identified as 33.5% and 16.7%, respectively.

Although the specific embodiments of the present invention have been described in detail, those skilled in the art will understand that various modifications and changes can be made to the details according to all the teachings that have been published, and these changes are within the protection scope of the present invention. All of the present invention is given by the appended claims and any equivalents thereof.

What is claimed is:

1. A delivery composition comprising a protein, wherein the protein is an effector protein in a CRISPR/Cas system and the protein comprises the amino acid sequence set forth in SEQ ID NO: 1 or SEQ ID NO: 2, and a delivery vehicle.

2. The delivery composition of claim 1, wherein the delivery vehicle is selected from the group consisting of a particle, a lipid particle, sugar particle, metal particle, protein particle, liposome, exosome, microvesicle, gene gun, and viral vector.

3. The delivery composition of claim 2, wherein the viral vector comprises replication defective retrovirus, lentivirus, adenovirus or adeno-associated virus.

4. An in vitro, isolated or in vivo cell or cell line or progeny thereof, the cell or cell line or the progeny thereof comprising a protein, wherein the protein is an effector protein in a CRISPR/Cas system and the protein comprises the amino acid sequence set forth in SEQ ID NO: 1 or SEQ ID NO: 2, wherein the cell is a eukaryotic cell.

5. The in vitro, isolated or in vivo cell or cell line or progeny thereof of claim 4, wherein the cell is an animal cell or a plant cell.

6. The in vitro, isolated or in vivo cell or cell line or progeny thereof of claim 5, wherein the cell is a stem cell.

* * * * *

```
                          SEQUENCE LISTING

<160> NUMBER OF SEQ ID NOS: 54

<210> SEQ ID NO 1
<211> LENGTH: 1045
<212> TYPE: PRT
<213> ORGANISM: artificial sequence
<220> FEATURE:
<223> OTHER INFORMATION: amino acid sequence of Cas12f.4

<400> SEQUENCE: 1

Met Lys Lys Val Glu Val Ser Arg Pro Tyr Gln Ser Leu Leu Leu Pro
1               5                   10                  15

Asn His Arg Lys Phe Lys Tyr Leu Asp Glu Thr Trp Asn Ala Tyr Lys
            20                  25                  30

Ser Val Lys Ser Leu Leu His Arg Phe Leu Val Cys Ala Tyr Gly Ala
        35                  40                  45

Val Pro Phe Asn Lys Phe Val Glu Val Val Glu Lys Val Asp Asn Asp
    50                  55                  60

Gln Leu Val Leu Ala Phe Ala Val Arg Leu Phe Arg Leu Val Pro Val
65                  70                  75                  80

Glu Ser Thr Ser Phe Ala Lys Val Asp Lys Ala Asn Leu Ala Lys Ser
                85                  90                  95

Leu Ala Asn His Leu Pro Val Gly Thr Ala Ile Pro Ala Asn Val Gln
            100                 105                 110

Ser Tyr Phe Asp Ser Asn Phe Asp Pro Lys Lys Tyr Met Trp Ile Asp
        115                 120                 125

Cys Ala Trp Glu Ala Asp Arg Leu Ala Arg Glu Met Gly Leu Ser Ala
        130                 135                 140

Ser Gln Phe Ser Glu Tyr Ala Thr Thr Met Leu Trp Glu Asp Trp Leu
145                 150                 155                 160

Pro Leu Asn Lys Asp Asp Val Asn Gly Trp Gly Ser Val Ser Gly Leu
            165                 170                 175

Phe Gly Glu Gly Lys Lys Glu Asp Arg Gln Gln Lys Val Lys Met Leu
            180                 185                 190

Asn Asn Leu Leu Asn Gly Ile Lys Lys Asn Pro Pro Lys Asp Tyr Thr
        195                 200                 205

Gln Tyr Leu Lys Ile Leu Leu Asn Ala Phe Asp Ala Lys Ser His Lys
    210                 215                 220

Glu Ala Val Lys Asn Tyr Lys Gly Asp Ser Thr Gly Arg Thr Ala Ser
225                 230                 235                 240
```

-continued

```
Tyr Leu Ser Glu Lys Ser Gly Glu Ile Thr Glu Leu Met Leu Glu Gln
                245                 250                 255

Leu Met Ser Asn Ile Gln Arg Asp Ile Gly Asp Lys Gln Lys Glu Ile
                260                 265                 270

Ser Leu Pro Lys Lys Asp Val Val Lys Lys Tyr Leu Glu Ser Glu Ser
                275                 280                 285

Gly Val Pro Tyr Asp Gln Asn Leu Trp Ser Gln Ala Tyr Arg Asn Ala
                290                 295                 300

Ala Ser Ser Ile Lys Lys Thr Asp Thr Arg Asn Phe Asn Ser Thr Leu
305                 310                 315                 320

Glu Lys Phe Lys Asn Glu Val Glu Leu Arg Gly Leu Leu Ser Glu Gly
                325                 330                 335

Asp Asp Val Glu Ile Leu Arg Ser Lys Phe Phe Ser Ser Glu Phe His
                340                 345                 350

Lys Thr Pro Asp Lys Phe Val Ile Lys Pro Glu His Ile Gly Phe Asn
                355                 360                 365

Asn Lys Tyr Asn Val Val Ala Glu Leu Tyr Lys Leu Lys Ala Glu Ala
                370                 375                 380

Thr Asp Phe Glu Ser Ala Phe Ala Thr Val Lys Asp Glu Phe Glu Glu
385                 390                 395                 400

Lys Gly Ile Lys His Pro Ile Lys Asn Ile Leu Glu Tyr Ile Trp Asn
                405                 410                 415

Asn Glu Val Pro Val Glu Lys Trp Gly Arg Val Ala Arg Phe Asn Gln
                420                 425                 430

Ser Glu Glu Lys Leu Leu Arg Ile Lys Ala Asn Pro Thr Val Glu Cys
                435                 440                 445

Asn Gln Gly Met Thr Phe Gly Asn Ser Ala Met Val Gly Glu Val Leu
                450                 455                 460

Arg Ser Asn Tyr Val Ser Lys Lys Gly Ala Leu Val Ser Gly Glu His
465                 470                 475                 480

Gly Gly Arg Leu Ile Gly Gln Asn Asn Met Ile Trp Leu Glu Met Arg
                485                 490                 495

Leu Leu Asn Lys Gly Lys Trp Glu Thr His His Val Pro Thr His Asn
                500                 505                 510

Met Lys Phe Phe Glu Glu Val His Ala Tyr Asn Pro Ser Leu Ala Asp
                515                 520                 525

Ser Val Asn Val Arg Asn Arg Leu Tyr Arg Ser Glu Asp Tyr Thr Gln
                530                 535                 540

Leu Pro Ser Ser Ile Thr Asp Gly Leu Lys Gly Asn Pro Lys Ala Lys
545                 550                 555                 560

Leu Leu Lys Arg Gln His Cys Ala Leu Asn Asn Met Thr Ala Asn Val
                565                 570                 575

Leu Asn Pro Lys Leu Ser Phe Thr Ile Asn Lys Lys Asn Asp Asp Tyr
                580                 585                 590

Thr Val Ile Ile Val His Ser Val Glu Val Ser Lys Pro Arg Arg Glu
                595                 600                 605

Val Leu Val Gly Asp Tyr Leu Val Gly Met Asp Gln Asn Gln Thr Ala
                610                 615                 620

Ser Asn Thr Tyr Ala Val Met Gln Val Val Lys Pro Lys Ser Thr Asp
625                 630                 635                 640

Ala Ile Pro Phe Arg Asn Met Trp Val Arg Phe Val Glu Ser Gly Ser
                645                 650                 655
```

-continued

```
Ile Glu Ser Arg Thr Leu Asn Ser Arg Gly Glu Tyr Val Asp Gln Leu
            660                 665                 670

Asn His Asp Gly Val Asp Leu Phe Glu Ile Gly Asp Thr Glu Trp Val
            675                 680                 685

Asp Ser Ala Arg Lys Phe Phe Asn Lys Leu Gly Val Lys His Lys Asp
        690                 695                 700

Gly Thr Leu Val Asp Leu Ser Thr Ala Pro Arg Lys Ala Tyr Ala Phe
705                 710                 715                 720

Asn Asn Phe Tyr Phe Lys Thr Met Leu Asn His Leu Arg Ser Asn Glu
                725                 730                 735

Val Asp Leu Thr Leu Leu Arg Asn Glu Ile Leu Arg Val Ala Asn Gly
            740                 745                 750

Arg Phe Ser Pro Met Arg Leu Gly Ser Leu Ser Trp Thr Thr Leu Lys
            755                 760                 765

Ala Leu Gly Ser Phe Lys Ser Leu Val Leu Ser Tyr Phe Asp Arg Leu
        770                 775                 780

Gly Ala Lys Glu Met Val Asp Lys Glu Ala Lys Asp Lys Ser Leu Phe
785                 790                 795                 800

Asp Leu Leu Val Ala Ile Asn Asn Lys Arg Ser Asn Lys Arg Glu Glu
                805                 810                 815

Arg Thr Ser Arg Ile Ala Ser Ser Leu Met Thr Val Ala Gln Lys Tyr
            820                 825                 830

Lys Val Asp Asn Ala Val Val His Val Val Val Glu Gly Asn Leu Ser
            835                 840                 845

Ser Thr Asp Arg Ser Ala Ser Lys Ala His Asn Arg Asn Thr Met Asp
        850                 855                 860

Trp Cys Ser Arg Ala Val Val Lys Lys Leu Glu Asp Met Cys Asn Leu
865                 870                 875                 880

Tyr Gly Phe Asn Ile Lys Gly Val Pro Ala Phe Tyr Thr Ser His Gln
                885                 890                 895

Asp Pro Leu Val His Arg Ala Asp Tyr Asp Asp Pro Lys Pro Ala Leu
            900                 905                 910

Arg Cys Arg Tyr Ser Ser Tyr Ser Arg Ala Asp Phe Ser Lys Trp Gly
            915                 920                 925

Gln Asn Ala Leu Ala Ala Val Val Arg Trp Ala Ser Asn Lys Lys Ser
        930                 935                 940

Asn Thr Cys Tyr Lys Val Gly Ala Val Glu Phe Leu Lys Gln His Gly
945                 950                 955                 960

Leu Phe Ala Asp Lys Lys Leu Thr Val Glu Gln Phe Leu Ser Lys Val
                965                 970                 975

Lys Asp Glu Glu Ile Leu Ile Pro Arg Arg Gly Gly Arg Val Phe Leu
            980                 985                 990

Thr Thr His Arg Leu Leu Ala Glu  Ser Thr Phe Val Tyr  Leu Asn Gly
        995                 1000                1005

Val Lys  Tyr His Ser Cys Asn  Ala Asp Glu Val Ala  Ala Val Asn
    1010                1015                1020

Ile Cys  Leu Asn Asp Trp Val  Ile Pro Cys Lys Lys  Lys Met Lys
    1025                1030                1035

Glu Glu  Ser Ser Ala Ser Gly
    1040                1045
```

<210> SEQ ID NO 2
<211> LENGTH: 1079
<212> TYPE: PRT

<213> ORGANISM: artificial sequence
<220> FEATURE:
<223> OTHER INFORMATION: amino acid sequence of Cas12f.5

<400> SEQUENCE: 2

Met Pro Lys Gln Lys Asp Leu Pro Tyr Ser Cys Leu Ser Tyr Leu Gln
1               5                   10                  15

Pro Asn Glu Arg Lys Leu Lys Leu Leu Asn Asn Thr Tyr Asp His Leu
            20                  25                  30

Thr His Gly Ser Lys Ile Met Phe Asp Thr Leu Ile Ala Leu Met Gly
        35                  40                  45

Gly Ile Asn Pro Lys Met Asp Val Ile Ser Glu Asn Lys Asp Ser Glu
    50                  55                  60

Ile Lys Asn Asn Arg Asp Pro Gln Thr Met Cys Ala Thr Ile Trp Phe
65                  70                  75                  80

Arg Pro Met Lys Ser Lys Arg Ile Asn Lys Val Trp Ser Pro Lys Gln
                85                  90                  95

Leu Lys Glu Gln Phe Leu Lys Tyr Tyr Gln Glu Tyr Glu Ala Asp Val
            100                 105                 110

Lys Ile Asn Asp Met Val Glu Ala Tyr Phe Asp Ser Pro Leu Gly Glu
            115                 120                 125

Asn Tyr Val Trp Val Asp Cys Arg Lys Lys Tyr Lys Gln Leu Val Lys
    130                 135                 140

Glu Leu Ala Ser Ile Ala Lys Thr Thr Glu Ala Asn Leu Lys Glu Asp
145                 150                 155                 160

Leu Asp Cys Asp Leu Glu Cys Leu Phe Arg Pro Ser Glu Lys Lys Met
            165                 170                 175

Lys Leu Tyr Gly Ser Asn Lys Ser Trp Ala Ile Ile Ser Asn Leu Phe
            180                 185                 190

Gly Glu Gly Asp Lys Glu Asp Arg Ser Lys Lys Ile Lys Ile Leu Thr
            195                 200                 205

Lys Ala Ile Gln Ile Leu Thr Glu Ser Asn Pro Glu Ser Tyr Ala Asp
    210                 215                 220

Val Gln Lys Ala Phe Leu Ala Ala Ala Asp Ile Asp Asp Pro Lys Lys
225                 230                 235                 240

Phe His Thr Gln Glu Ile Trp Gly Asn Gly Ser Pro Gly Asn Ile Val
            245                 250                 255

Lys Met Ala Arg Gly Asp Phe Leu Gly Lys Glu Phe Asp Cys Glu Lys
            260                 265                 270

Ile Leu Glu Lys Ile Asn Asp Val Leu Lys Glu Lys Thr Leu Asp Phe
            275                 280                 285

Asp Leu Lys Val Arg Leu Ser Phe Lys Glu Tyr Leu Ile Ser Lys Ile
    290                 295                 300

Gly His Tyr Tyr Gln Asn Ser Trp Ser Glu Met Ile Asn Ser Ala Phe
305                 310                 315                 320

Ala Asp Ile Ile Ser Lys Asn Thr Arg Asn Val Asn Phe Ala Lys Glu
            325                 330                 335

Lys Val Gln Leu Gln Lys Thr Leu Ser Glu Thr Ser Asn Ala Lys Val
            340                 345                 350

Glu Leu Leu Thr Asp Phe Phe Lys Ser Asp Phe Phe Leu Gly Asp Asp
            355                 360                 365

Lys Phe Asp Ile Ala Pro His Asn Leu Gly Gly Ala Asn Gly Ile Lys
    370                 375                 380

Phe Phe Tyr Asp Phe Cys Lys Lys Asn Glu Asp Gln Tyr Phe Leu Glu

-continued

```
385                 390                 395                 400

Glu Leu Leu Leu Glu Ala Ala Ile Glu Glu Ser Val Ala Glu Ala Lys
                405                 410                 415

Ser Lys Ser Leu Lys Glu Pro His Lys Asp Leu Leu Arg Tyr Val Phe
                420                 425                 430

Ser Ile Arg Lys Glu Thr Thr Phe Glu Glu Leu Arg Asp Ala Ala Lys
            435                 440                 445

Tyr Ile Gln Thr His Lys Arg Ile Lys Asn Met Ser Val His Pro Thr
        450                 455                 460

Val Lys Ser Asp Ile Gly Phe Asn Val Thr Ser Gly Ser Ala Leu Val
465                 470                 475                 480

Gly His Val Val Ser Pro Ser Lys Lys Ile Asn Gly Arg Ile Ala Gly
                485                 490                 495

Glu Ser Gly Phe Ile Trp Ile Cys Met Lys Leu Trp Glu Gly Gly Asp
                500                 505                 510

Lys Trp Ile Glu His His Ile Pro Phe Thr Asp Thr Arg Phe Tyr Glu
            515                 520                 525

Gln Ile Tyr Lys Tyr Asn Pro Asp Ser Lys Leu Glu Pro Val Val Leu
        530                 535                 540

Arg Thr Lys Arg Tyr Gly Val Asp Leu Thr Lys Phe Asn Leu Pro Pro
545                 550                 555                 560

Met Lys Thr Asp Leu Lys His Val Ala Pro Lys Glu Lys Asn Lys His
                565                 570                 575

Asn Tyr Val Lys Val Gln Arg Arg Leu Gln Arg Leu Asn His Pro Asp
                580                 585                 590

Val Pro Asn Thr Ile Trp Pro Lys Ser Asn Ile Gly Phe Thr Ile Arg
            595                 600                 605

Arg Lys Asn Gly Lys Tyr Ile Leu Asn Val Val His Lys Leu Pro Lys
        610                 615                 620

Asn Lys Val Lys Lys Ser Val Lys Pro Lys Phe Gly Asp Ile Leu Ile
625                 630                 635                 640

Gly Val Asp Gln Asn Gln Thr Thr Asn His Thr Cys Ser Ile Tyr Lys
                645                 650                 655

Val Val Lys Lys Asn Thr Lys Glu Ala Leu Leu Val Pro Glu Ser Asp
                660                 665                 670

Phe Tyr Leu Lys Lys Ile Glu Thr Ile Lys Val Thr Ser Phe Thr Lys
                675                 680                 685

Ala Arg Tyr Asn Ser Glu Pro Ile Asp Gln Leu His Tyr Glu Gly Ile
        690                 695                 700

Ser Val Asp Asn Glu Val Phe Lys Asn Trp Cys Lys Asp Arg Glu Gln
705                 710                 715                 720

Phe Val Asp Ser Leu Ser Ile Lys Glu Phe Lys Asn Glu Phe Lys Arg
                725                 730                 735

Ile Lys Asn Lys Asn Glu Asn Leu Tyr Ser Phe Asn Ala Asp Tyr Leu
            740                 745                 750

Trp Leu Leu Lys Arg Ile Ile Ser Gly Lys Leu Asn Lys Lys Lys Phe
            755                 760                 765

Asp Val Ser Val Phe Glu Lys Ser Ile Arg Asn Glu Ile Leu Ala Met
        770                 775                 780

Cys Ser Lys Glu Gly Leu Gly Pro Leu Arg Val Ser Ser Leu Ser Ser
785                 790                 795                 800

Asn Ser Leu Lys Ser Ile Gly Phe Leu Lys Ser Ala Ile Cys Ser Phe
                805                 810                 815
```

Ile Ser Ile Ala Leu Asn Arg Lys Gly Ile Glu Asp Lys Thr Asp Val
            820                 825                 830

Gln Lys Asn Lys Ile Asp Pro Glu Leu Phe Asp Leu Ile Gly Lys Ile
            835                 840                 845

Glu Gln Lys Arg Val Asn Lys Arg Met Glu Lys Thr Arg Arg Asn Ala
    850                 855                 860

Asp Phe Ile Leu Thr Met Ala Val Asp Tyr Gln Lys Ser Ser Gln Lys
865                 870                 875                 880

Asn Val Phe Leu Phe Cys Glu Gly Asn Leu Glu Thr Ala Lys Thr Gly
                885                 890                 895

Asn Ser Lys Lys Arg Asn Ser Ala Asn Val Asp Trp Cys Ser Arg Lys
            900                 905                 910

Leu Phe Asp Phe Leu Lys Glu Lys Ser Leu Arg His Gly Ile Tyr Phe
            915                 920                 925

His Ala Val Thr Pro His Tyr Thr Ser His Gln Asp Pro Phe Glu Tyr
    930                 935                 940

His Pro Ser Asn Lys Val Met Leu Pro Arg Phe Ala Lys Phe Asp Lys
945                 950                 955                 960

Asn Asn Pro Ile Gln Asp Trp Ala Glu Lys Lys Tyr Leu Gly Phe Ala
                965                 970                 975

Asn Ser Asp Pro Glu Ser Gly Thr Ala Leu Tyr Tyr Lys Lys Gly Val
            980                 985                 990

Glu Asn Phe Phe Ala His Tyr Gln  Lys Gly Phe Lys Glu  Lys Val Glu
        995                 1000                 1005

Leu Ala  Glu Met Lys Asn Val  Leu Asn Ser Asn Leu  Lys Asn Gly
    1010                1015                 1020

Asn Leu  Glu His Val Phe Cys  Pro Ile Arg Gly Gly  Arg Tyr Tyr
    1025                1030                 1035

Leu Ser  Thr His Pro Val Thr  Ser Asp Ala Lys Pro  Phe Glu Phe
    1040                1045                 1050

Asn Gly  Arg Lys Cys Tyr Ile  Cys Asp Ser Asp Glu  Val Ala Ala
    1055                1060                 1065

Thr Asn  Ile Met Leu Ile Gly  Leu Phe Tyr Val
    1070                1075

<210> SEQ ID NO 3
<211> LENGTH: 1054
<212> TYPE: PRT
<213> ORGANISM: artificial sequence
<220> FEATURE:
<223> OTHER INFORMATION: amino acid sequence of Cas12f.6

<400> SEQUENCE: 3

Met Ser Ser Ala Ile Lys Ser Tyr Lys Ser Val Leu Arg Pro Asn Glu
1               5                   10                  15

Arg Lys Asn Gln Leu Leu Lys Ser Thr Ile Gln Cys Leu Glu Asp Gly
            20                  25                  30

Ser Ala Phe Phe Phe Lys Met Leu Gln Gly Leu Phe Gly Gly Ile Thr
        35                  40                  45

Pro Glu Ile Val Arg Phe Ser Thr Glu Gln Glu Lys Gln Gln Gln Asp
    50                  55                  60

Ile Ala Leu Trp Cys Ala Val Asn Trp Phe Arg Pro Val Ser Gln Asp
65                  70                  75                  80

Ser Leu Thr His Thr Ile Ala Ser Asp Asn Leu Val Glu Lys Phe Glu
                85                  90                  95

-continued

```
Glu Tyr Tyr Gly Gly Thr Ala Ser Asp Ala Ile Lys Gln Tyr Phe Ser
            100                 105                 110

Ala Ser Ile Gly Glu Ser Tyr Tyr Trp Asn Asp Cys Arg Gln Gln Tyr
            115                 120                 125

Tyr Asp Leu Cys Arg Glu Leu Gly Val Glu Val Ser Asp Leu Thr His
        130                 135                 140

Asp Leu Glu Ile Leu Cys Arg Glu Lys Cys Leu Ala Val Ala Thr Glu
145                 150                 155                 160

Ser Asn Gln Asn Ser Ile Ile Ser Val Leu Phe Gly Thr Gly Glu
                165                 170                 175

Lys Glu Asp Arg Ser Val Lys Leu Arg Ile Thr Lys Lys Ile Leu Glu
            180                 185                 190

Ala Ile Ser Asn Leu Lys Glu Ile Pro Lys Asn Val Ala Pro Ile Gln
            195                 200                 205

Glu Ile Ile Leu Asn Val Ala Lys Ala Thr Lys Glu Thr Phe Arg Gln
        210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
        290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
            325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
            355                 360                 365

Ala Trp Glu Asp Asp Pro Ala Asp Pro Glu Asn Ala Ile Val Val Leu
        370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
            435                 440                 445

Ala Val Ile Leu Pro Glu Lys Ala Gln Arg Asn Asp Arg Pro Asn Ser
        450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510
```

-continued

```
Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
        530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Asp Val Gly Arg Gln Lys Gly Thr Leu Gln Ile Gly
                580                 585                 590

Asp Arg Phe Cys Gly Tyr Asp Gln Asn Gln Thr Ala Ser His Ala Tyr
                595                 600                 605

Ser Leu Trp Glu Val Val Lys Glu Gly Gln Tyr His Lys Glu Leu Gly
        610                 615                 620

Cys Phe Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
                660                 665                 670

Trp Gln Ile Thr Lys Lys Asn Lys Lys Glu Ile Val Thr Val Glu
        675                 680                 685

Ala Lys Glu Lys Phe Asp Ala Ile Cys Lys Tyr Gln Pro Arg Leu Tyr
        690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
                740                 745                 750

Thr Leu Glu Thr Val Lys Ala Val Lys Gly Ile Ile Tyr Ser Tyr Phe
        755                 760                 765

Ser Thr Ala Leu Asn Ala Ser Lys Asn Asn Pro Ile Ser Asp Glu Gln
        770                 775                 780

Arg Lys Glu Phe Asp Pro Glu Leu Phe Ala Leu Leu Glu Lys Leu Glu
785                 790                 795                 800

Leu Ile Arg Thr Arg Lys Lys Lys Gln Lys Val Glu Arg Ile Ala Asn
                805                 810                 815

Ser Leu Ile Gln Thr Cys Leu Glu Asn Asn Ile Lys Phe Ile Arg Gly
        820                 825                 830

Glu Gly Asp Leu Ser Thr Thr Asn Asn Ala Thr Lys Lys Lys Ala Asn
        835                 840                 845

Ser Arg Ser Met Asp Trp Leu Ala Arg Gly Val Phe Asn Lys Ile Arg
        850                 855                 860

Gln Leu Ala Pro Met His Asn Ile Thr Leu Phe Gly Cys Gly Ser Leu
865                 870                 875                 880

Tyr Thr Ser His Gln Asp Pro Leu Val His Arg Asn Pro Asp Lys Ala
                885                 890                 895

Met Lys Cys Arg Trp Ala Ala Ile Pro Val Lys Asp Ile Gly Asp Trp
                900                 905                 910

Val Leu Arg Lys Leu Ser Gln Asn Leu Arg Ala Lys Asn Ile Gly Thr
        915                 920                 925

Gly Glu Tyr Tyr His Gln Gly Val Lys Glu Phe Leu Ser His Tyr Glu
```

-continued

```
        930               935               940
Leu Gln Asp Leu Glu Glu Glu Leu Leu Lys Trp Arg Ser Asp Arg Lys
945               950               955               960

Ser Asn Ile Pro Cys Trp Val Leu Gln Asn Arg Leu Ala Glu Lys Leu
                  965               970               975

Gly Asn Lys Glu Ala Val Val Tyr Ile Pro Val Arg Gly Gly Arg Ile
                  980               985               990

Tyr Phe Ala Thr His Lys Val Ala  Thr Gly Ala Val Ser  Ile Val Phe
          995               1000               1005

Asp Gln  Lys Gln Val Trp Val  Cys Asn Ala Asp His  Val Ala Ala
     1010               1015               1020

Ala Asn  Ile Ala Leu Thr Val  Lys Gly Ile Gly Glu  Gln Ser Ser
     1025               1030               1035

Asp Glu  Glu Asn Pro Asp Gly  Ser Arg Ile Lys Leu  Gln Leu Thr
     1040               1045               1050

Ser
```

```
<210> SEQ ID NO 4
<211> LENGTH: 3138
<212> TYPE: DNA
<213> ORGANISM: artificial sequence
<220> FEATURE:
<223> OTHER INFORMATION: encoding nucleic acid sequence of Cas12f.4

<400> SEQUENCE: 4
atgaagaagg tcgaggtgtc gcggccatac cagagcctgc tcctgccaaa ccaccggaag      60
ttcaagtacc tcgacgagac ctggaatgcg tacaagtccg ttaagagcct gctccaccgc     120
ttcctggtgt gcgcttacgg cgctgttccc ttcaacaagt tcgtggaggt tgtcgagaag     180
gttgataacg accagctcgt gctggctttc gcggtgcgcc tcttccgcct ggtccccgtg     240
gagagcacct ctttcgccaa ggttgacaag gccaatctgg cgaagtccct ggccaatcac     300
ctgcctgtgg gcacagccat tcctgccaat gttcagtcct acttcgattc aaatttcgac     360
cccaagaagt acatgtggat cgactgcgcg tgggaggctg atcgcctggc tcgggagatg     420
ggcctgagcg cgagccagtt ctctgagtac gcgactacaa tgctctggga ggactggctg     480
cccctcaata aggatgatgt gaacggctgg gggtccgtgt cggggctctt cggcgagggc     540
aagaaggagg accggcagca gaaggtgaag atgctgaata acctgctgaa tggcatcaag     600
aagaatccgc ccaaggatta cacccagtac ctgaagatcc tcctgaacgc gttcgacgcg     660
aagtcgcaca aggaggctgt taagaactac aaggggggact ctacgggggcg caccgcgtct     720 tacctgtcag agaagtctgg cgagatcaca gagctgatgc tcgagcagct gatgtcaaac     780
atccagaggg atattggcga caagcagaag gagatctccc tgccgaagaa ggacgtggtc     840
aagaagtacc tcgagtcaga gtccggcgtc ccatacgatc agaacctgtg gtcccaggcc     900
taccgcaacg ctgccagctc gatcaagaag actgatacgc ggaacttcaa ctccactctc     960
gagaagttca gaatgaggt ggagctgagg ggcctgctga gcgagggcga cgacgttgag    1020
atcctgaggt ctaagttctt cagcagcgag ttccacaaga ccctgataa gttcgttatt    1080 aagccagagc atattgggtt caacaataag tacaatgtcg ttgccgagct gtacaagctc    1140
aaggctgagg cgaccgattt cgagagcgct ttcgccacag tcaaggatga gttcgaggag    1200
aagggcatca gcacccaat caagaacatc ctcgagtaca tctggaataa cgaggtgccc    1260
gtcgagaagt ggggccgggt tgcccgcttc aaccagtccg aggagaagct cctccggatt    1320
```

-continued

```
aaggccaacc ccacggtgga gtgcaaccag ggcatgacct tcggcaattc cgcgatggtt    1380
ggcgaggtcc tcaggtccaa ctacgtctct aagaagggcg cgctggtgtc cggcgagcac    1440
ggcgggcgcc tgatcggcca gaacaatatg atctggctgg agatgcggct gctcaacaag    1500
gggaagtggg agacccacca cgttccaacc cataacatga agttcttcga ggaggtgcat    1560
gcctacaatc cctctctggc ggattctgtt aacgtgcgga atcggctgta ccgctcagag    1620
gactacaccc agctgccttc aagcattacc gacgggctga agggcaatcc gaaggcgaag    1680
ctcctgaagc gccagcactg cgctctgaac aatatgacag ctaatgttct caatcctaag    1740
ctgagcttca cgatcaacaa gaagaacgat gattacacgg tcatcattgt ccatagcgtt    1800
gaggtctcga agcctcggag ggaggtgctc gttggcgatt acctcgtggg catggaccag    1860
aatcagacag cgtctaatac atacgccgtc atgcaggtcg tcaagccgaa gtctacagat    1920
gcgatcccgt tccgcaacat gtgggtgcgg ttcgtggagt cagggtctat cgagtcccgg    1980
accctcaaca gccgcgggga gtatgttgat cagctgaatc atgacggcgt ggacctcttc    2040
gagatcggcg atacggagtg ggtggactcc gcgcggaagt tcttcaataa gctcggcgtt    2100
aagcacaagg atggcacact ggttgatctg tctacggcgc cccggaaggc ctacgctttc    2160
aacaacttct acttcaagac catgctgaat catctccgga gcaatgaggt tgacctgacg    2220
ctcctgcgca atgagatcct ccgggttgcc aatgggcggt tctccccgat gcgcctcggc    2280
tcgctctcct ggactactct caaggccctg ggctcgttca agtccctggt gctgtcgtac    2340
ttcgaccggc tgggcgccaa ggagatggtc gacaaggagg ctaaggataa gtctctcttc    2400
gacctcctcg tggctatcaa caacaagcgc tctaataagc gcgaggagcg gacttcccgg    2460
attgcctcca gcctcatgac tgtggcgcag aagtacaagg ttgataacgc tgtggtccat    2520
gtggtcgtcg aggggaatct ctccagcacg gacaggagcg cgtcaaaggc ccataatcgg    2580
aacactatgg attggtgctc tagggccgtg gtgaagaagc tggaggacat gtgcaatctc    2640
tacggcttca atatcaaggg cgtcccagcc ttctacacat cccaccagga cccgctcgtc    2700
caccgcgccg actacgatga ccctaagccg gcgctcaggt gccgctactc ctcgtactca    2760
agggcggact tcagcaagtg ggggcagaac gctctcgcgg cggtggttcg ctgggcgtct    2820
aataagaagt ccaacacctg ctacaaggtc ggggccgtgg agttcctcaa gcagcacggc    2880
ctcttcgcgg acaagaagct gacagtcgag cagttcctct cgaaggtgaa ggacgaggag    2940
atcctcattc cccgcagggg cgggagggtg ttcctcacaa ctcaccggct cctggcggag    3000
tccactttcg tgtacctgaa cggcgttaag taccattcat gcaacgccga tgaggtggcg    3060
gctgttaaca tctgcctgaa tgactgggtt atcccgtgca agaagaagat gaaggaggag    3120
tcaagcgcgt ccgggtag                                                   3138
```

<210> SEQ ID NO 5
<211> LENGTH: 3240
<212> TYPE: DNA
<213> ORGANISM: artificial sequence
<220> FEATURE:
<223> OTHER INFORMATION: encoding nucleic acid sequence of Cas12f.5

<400> SEQUENCE: 5

```
atgccgaagc agaaggacct cccctactcc tgcctgagct acctccagcc gaacgagagg     60
aagctcaagc tcctgaacaa cacctacgac cacctgacgc acggcagcaa gatcatgttc    120
gacaccctga tcgcgctcat gggcggcatc aaccccaaga tggacgtgat ctccgagaac    180
aaggacagcg agatcaagaa caaccgcgac ccgcagacca tgtgcgccac gatctggttc    240
```

-continued

```
cgccccatga agtccaagag gatcaacaag gtctggagcc cgaagcagct caaggagcag       300
ttcctgaagt actaccagga gtacgaggcg gacgtgaaga tcaacgacat ggtcgaggcc       360
tacttcgact ccccgctcgg cgagaactac gtgtgggtcg actgcaggaa gaagtacaag       420
cagctggtga aggagctggc ctccatcgcc aagaccacgg aggccaacct gaaggaggac       480
ctcgactgcg acctggagtg cctcttccgc cccagcgaga agaagatgaa gctctacggc       540
tccaacaaga gctgggcgat catctccaac ctgttcggcg agggcgacaa ggaggacagg       600
agcaagaaga tcaagatcct caccaaggcc atccagatcc tgacggagtc caaccccgag       660
agctacgccg acgtgcagaa ggccttcctc gctgccgcgg acatcgacga cccgaagaag       720
ttccacacgc aggagatctg gggcaacggc agccccggca acatcgtcaa gatggcccgc       780
ggcgacttcc tgggcaagga gttcgactgc gagaagatcc tcgagaagat caacgacgtg       840
ctgaaggaga agacgctgga cttcgacctc aaggtcaggc tgtccttcaa ggagtacctc       900
atcagcaaga tcggccacta ctaccagaac tcctggagcg agatgatcaa ctccgcgttc       960
gccgacatca tcagcaagaa cacccgcaac gtgaacttcg cgaaggagaa ggtccagctc      1020
cagaagaccc tgtccgagac gagcaacgcc aaggtggagc tgctgacgga cttcttcaag      1080
tccgacttct tcctcggcga cgacaagttc gacatcgcgc cgcacaacct gggcggcgcc      1140
aacggcatca agttcttcta cgatttctgc aagaagaacg aggatcagta cttcctcgag      1200
gagctgctgc tcgaggccgc tatcgaggag tcggtggccg aggccaagtc caagagcctg      1260
aaggagcccc acaaggacct gctccgctac gtcttcagca ttaggaagga gacgaccttc      1320
gaggagctga gggacgccgc caagtacatc cagacccaca gaggatcaa gaacatgtcc       1380 gtgcacccga ccgtcaagag cgacatcggc ttcaacgtga cgtccggcag cgcgctcgtc      1440
ggccacgtcg tgtcccccag caagaagatc aacggcagga tcgcgggcga gagcggcttc      1500
atctggatct gcatgaagct gtgggagggc ggcgacaagt ggatcgagca ccacatcccg      1560
ttcaccgaca cgaggttcta cgagcagatc tacaagtaca acccggactc caagctcgag      1620
cccgtggtcc tgcgcaccaa gcgctacggc gtggacctca cgaagttcaa cctgccgccc      1680
atgaagacgg acctcaagca cgtcgccccg aaggagaaga acaagcacaa ctacgtgaag      1740
gtgcagaggc ggctccagag gctcaaccac cccgacgtgc ccaacaccat ctggcccaag      1800
agcaacatcg gcttcacgat ccgcaggaag aacggcaagt acatcctcaa cgtggtccac      1860
aagctgccga agaacaaggt gaagaagtcc gtcaagccca agttcggcga catcctgatc      1920
ggcgtcgacc agaaccagac cacgaaccac acctgctcca tctacaaggt ggtcaagaag      1980
aacaccaagg aggcgctgct cgtgccggag agcgacttct acctcaagaa gatcgagacc      2040
atcaaggtca cctccttcac gaaggccagg tacaacagcg agcccatcga ccagctgcac      2100
tacgagggca tctccgtgga caacgaggtc ttcaagaact ggtgcaagga ccgcgagcag      2160
ttcgtggact ccctcagcat caaggagttc aagaacgagt tcaagaggat caagaacaag      2220
aacgagaacc tctactcctt caacgcggac tacctgtggc tgctcaagcg catcatcagc      2280
ggcaagctca acaagaagaa gttcgacgtg tccgtcttcg agaagagcat ccgcaacgag      2340
atcctggcta tgtgctccaa ggagggcctg gcccccctca gggtctccag cctctccagc      2400
aactccctga agagcatcgg cttcctcaag tccgcgatct gctccttcat cagcatcgcc      2460
ctgaacagga gggcatcga ggacaagacc gacgtgcaga agaacaagat cgaccccgag       2520
ctgttcgacc tcatcggcaa gatcgagcag aagcgcgtca caagaggat ggagaagacc       2580
```

```
cgcaggaacg cggacttcat cctcacgatg gccgtggact accagaagtc cagccagaag    2640
aacgtcttcc tcttctgcga gggcaacctg gagaccgcga agacgggcaa ctccaagaag    2700
cgcaacagcg ccaacgtgga ctggtgctcc aggaagctct tcgacttcct gaaggagaag    2760
agcctccgcc acggcatcta cttccacgcg gtgacccccgc actacacgtc ccaccaggac    2820
ccgttcgagt accaccccag caacaaggtc atgctgccga ggttcgccaa gttcgacaag    2880
aacaacccca tccaggactg ggcggagaag aagtacctcg gcttcgccaa ctccgacccc    2940
gagtcgggca ccgcgctgta ctacaagaag ggcgtcgaga acttcttcgc ccactaccag    3000
aagggcttca aggagaaggt ggagctggcg gagatgaaga acgtcctcaa cagcaacctg    3060
aagaacggca acctcgagca cgtcttctgc ccgatcaggg gcggcaggta ctacctgtcg    3120 acgcacccccg tcacgagcga cgctaagccc ttcgagttca acggccgcaa gtgctacatc    3180
tgcgactccg acgaggtggc ggccaccaac atcatgctga tcggcctctt ctacgtgtga    3240
```

```
<210> SEQ ID NO 6
<211> LENGTH: 3165
<212> TYPE: DNA
<213> ORGANISM: artificial sequence
<220> FEATURE:
<223> OTHER INFORMATION: encoding nucleic acid sequence of Cas12f.6

<400> SEQUENCE: 6
```

```
atgtccagcg ccatcaagtc ctacaagagc gtgctgcgcc ccaacgagag gaagaaccag      60
ctcctgaagt ccaccatcca gtgcctcgag gacggcagcg ccttcttctt caagatgctg     120
cagggcctct tcggtggcat cacccccgag atcgtcaggt tctccacgga gcaggagaaa     180
cagcagcagg acatcgccct gtggtgcgcc gtcaactggt tcaggcccgt gtcccaggac     240 agcctcacccc acacgatcgc cagcgacaac ctggtggaga agttcgagga gtactacggc     300
ggcacggcct ccgacgcgat caagcagtac ttctccgcga gcatcggcga gagctactac     360
tggaacgact gcaggcagca gtactacgac ctgtgcaggg agctgggcgt ggaggtctcc     420 gacctgacccc acgacctgga gatcctgtgc agggagaagt gcctggcggt ggccaccgag     480
agcaaccaga caaactccat catcagcgtc ctgttcggca ccggcgagaa ggaggacagg     540
tccgtgaagc tcaggatcac gaagaagatc ctcgaggcca tcagcaacct gaaggagatc     600
ccgaagaacg tcgcgcccat ccaggagatc atcctgaacg tggccaaggc gaccaaggag     660
acgttcaggc aggtgtacgc gggcaacctc ggcgcccccat ccaccctgga gaagttcatc     720
gccaaggacg gccagaagga gttcgacctg aagaagctcc agacggacct caagaaggtc     780
atccgcggca gtccaaggga gagggactgg tgctgccagg aggagctgcg cagctacgtg     840
gagcagaaca ccatccagta cgacctctgg gcctggggcg agatgttcaa caaggcccac     900
accgcgctca agatcaagtc cacgaggaac tacaacttcg cgaagcagcg cctcgagcag     960
ttcaaggaga tccagagcct gaacaacctc ctggtggtca agaagctcaa cgacttcttc    1020
gactccgagt tcttcagcgg cgaggagacc tacacgatct gcgtgcacca cctgggcggc    1080
aaggacctgt ccaagctcta caaggcctgg gaggacgacc ccgccgaccc cgagaacgcg    1140
atcgtggtcc tgtgcgacga cctcaagaac aacttcaaga aggagccgat ccgcaacatc    1200
ctcaggtaca tcttcaccat caggcaggag tgctcggctc aggacatcct ggcggccgcc    1260
aagtacaacc agcagctcga ccgctacaag tcccagaagg ccaacccatc ggtcctgggc    1320
aaccagggct tcacctggac gaacgccgtg atcctgcccg agaaggccca gaggaacgac    1380
aggcccaact ccctcgacct gaggatctgg ctctacctga agctcaggca ccccgacggc    1440
```

-continued

```
aggtggaaga agcaccacat ccccttctac gacacccgct tcttccagga gatctacgcc      1500
gcgggcaaca gccccgtgga cacctgccag ttccgcacgc cgaggttcgg ctaccacctg      1560
cccaagctca ccgaccagac ggccatcagg gtcaacaaga agcacgtcaa ggccgctaag      1620
acggaggctc gcatcaggct ggcgatccag cagggcacgc tcccggtgtc caacctgaag      1680
atcaccgaga tctccgcgac gatcaacagc aagggccagg tgcgcatccc ggtcaagttc      1740
gacgtgggca ggcagaaggg caccctccag atcggcgacc gcttctgcgg ctacgaccag      1800
aaccagaccg cctcccacgc ctacagcctg tgggaggtgg tcaaggaggg ccagtaccac      1860
aaggagctgg gctgcttcgt caggttcatc tccagcggcg acatcgtgtc catcaccgag      1920
aaccgcggca accagttcga ccagctcagc tacgagggcc tggcctaccc ccagtacgcc      1980
gactggagga agaaggcctc caagttcgtg agcctgtggc agatcaccaa gaagaacaag      2040
aagaaggaga tcgtgacggt cgaggccaag gagaagttcg acgcgatctg caagtaccag      2100
ccgcgcctct acaagttcaa caaggagtac gcctacctcc tgcgcgacat cgtcaggggc      2160
aagagcctgg tggagctgca gcagatccgc caggagatct tcaggttcat cgagcaggac      2220
tgcggcgtca cgcgcctggg ctccctgagc ctctccaccc tggagacggt gaaggccgtc      2280
aagggcatca tctactccta cttcagcacg gccctgaacg cgtccaagaa caacccgatc      2340
agcgacgagc agcgcaagga gttcgacccc gagctgttcg ccctcctgga gaagctggag      2400
ctgatccgca cccgcaagaa gaagcagaag gtggagagga tcgcgaactc cctcatccag      2460
acgtgcctgg agaacaacat caagttcatc cgcggcgagg gcgacctgag caccacgaac      2520
aacgccacca agaagaaggc gaacagccgc agcatggact ggctggccag gggcgtcttc      2580
aacaagatcc gccagctcgc gccgatgcac aacatcaccc tcttcggctg cggctccctg      2640
tacacgagcc accaggaccc gctcgtgcac aggaaccccg acaaggccat gaagtgcagg      2700
tgggccgcta tcccggtcaa ggacatcggc gactgggtgc tgaggaagct ctcccagaac      2760
ctgcgcgcga agaacatcgg cacgggcgag tactaccacc agggcgtcaa ggagttcctc      2820
agccactacg agctgcagga cctcgaggag gagctgctga agtggcgctc cgacaggaag      2880
agcaacatcc cctgctgggt gctgcagaac cgcctcgccg agaagctggg caacaaggag      2940
gccgtggtct acatccccgt ccgcggcggc aggatctact tcgctaccca caaggtggct      3000
accgcgcgcg tgtccatcgt cttcgaccag aagcaagtgt gggtctgcaa cgcggaccac      3060
gtcgccgctg ccaacatcgc cctgaccgtg aagggcatcg gcgagcagtc cagcgacgag      3120
gagaacccgg acggcagcag gatcaagctg cagctcacca gctga                     3165
```

<210> SEQ ID NO 7
<211> LENGTH: 63
<212> TYPE: RNA
<213> ORGANISM: artificial sequence
<220> FEATURE:
<223> OTHER INFORMATION: Cas12f.4/prototype direct repeat

<400> SEQUENCE: 7

```
cucugaccac cugagagaau gugugcauag ucacacggua uaacaacuuc gacgagcucu      60
aca                                                                    63
```

<210> SEQ ID NO 8
<211> LENGTH: 63
<212> TYPE: RNA
<213> ORGANISM: artificial sequence
<220> FEATURE:

-continued

<223> OTHER INFORMATION: Cas12f.5/prototype direct repeat

<400> SEQUENCE: 8
auaacaauag auagaaaaug ugucauacua cgacacggua uaacaacuuc gacgagcucu          60
aca                                                                       63

<210> SEQ ID NO 9
<211> LENGTH: 54
<212> TYPE: RNA
<213> ORGANISM: artificial sequence
<220> FEATURE:
<223> OTHER INFORMATION: Cas12f.6/prototype direct repeat

<400> SEQUENCE: 9
ccuaagaaau ccgucuuuca uugacgggu auaacaacuu cgacgagcuc uaca               54

<210> SEQ ID NO 10
<211> LENGTH: 63
<212> TYPE: DNA
<213> ORGANISM: artificial sequence
<220> FEATURE:
<223> OTHER INFORMATION: encoding nucleic acid sequence of
      Cas12f.4/prototype direct repeat

<400> SEQUENCE: 10
ctctgaccac ctgagagaat gtgtgcatag tcacacggta taacaacttc gacgagctct          60
aca                                                                       63

<210> SEQ ID NO 11
<211> LENGTH: 63
<212> TYPE: DNA
<213> ORGANISM: artificial sequence
<220> FEATURE:
<223> OTHER INFORMATION: encoding nucleic acid sequence of
      Cas12f.5/prototype direct repeat

<400> SEQUENCE: 11
ataacaatag atagaaaatg tgtcatacta cgacacggta taacaacttc gacgagctct          60
aca                                                                       63

<210> SEQ ID NO 12
<211> LENGTH: 54
<212> TYPE: DNA
<213> ORGANISM: artificial sequence
<220> FEATURE:
<223> OTHER INFORMATION: encoding nucleic acid sequence of
      Cas12f.6/prototype direct repeat

<400> SEQUENCE: 12
cctaagaaat ccgtctttca ttgacggggt ataacaactt cgacgagctc taca               54

<210> SEQ ID NO 13
<211> LENGTH: 23
<212> TYPE: RNA
<213> ORGANISM: artificial sequence
<220> FEATURE:
<223> OTHER INFORMATION: Cas12f.4/mature direct repeat

<400> SEQUENCE: 13
agagaaugug ugcauaguca cac                                                 23

<210> SEQ ID NO 14
<211> LENGTH: 24
<212> TYPE: RNA

-continued

```
<213> ORGANISM: artificial sequence
<220> FEATURE:
<223> OTHER INFORMATION: Cas12f.5/mature direct repeat

<400> SEQUENCE: 14
agaaaaugug ucauacuacg acac                                    24

<210> SEQ ID NO 15
<211> LENGTH: 23
<212> TYPE: RNA
<213> ORGANISM: artificial sequence
<220> FEATURE:
<223> OTHER INFORMATION: Cas12f.6/mature direct repeat

<400> SEQUENCE: 15
agaaauccgu cuuucauuga cgg                                     23

<210> SEQ ID NO 16
<211> LENGTH: 23
<212> TYPE: DNA
<213> ORGANISM: artificial sequence
<220> FEATURE:
<223> OTHER INFORMATION: encoding nucleic acid sequence of
      Cas12f.4/mature direct repeat

<400> SEQUENCE: 16
agagaatgtg tgcatagtca cac                                     23

<210> SEQ ID NO 17
<211> LENGTH: 24
<212> TYPE: DNA
<213> ORGANISM: artificial sequence
<220> FEATURE:
<223> OTHER INFORMATION: encoding nucleic acid sequence of
      Cas12f.5/mature direct repeat

<400> SEQUENCE: 17
agaaaatgtg tcatactacg acac                                    24

<210> SEQ ID NO 18
<211> LENGTH: 23
<212> TYPE: DNA
<213> ORGANISM: artificial sequence
<220> FEATURE:
<223> OTHER INFORMATION: encoding nucleic acid sequence of
      Cas12f.6/mature direct repeat

<400> SEQUENCE: 18
agaaatccgt ctttcattga cgg                                     23

<210> SEQ ID NO 19
<211> LENGTH: 11
<212> TYPE: PRT
<213> ORGANISM: artificial sequence
<220> FEATURE:
<223> OTHER INFORMATION: NLS sequence

<400> SEQUENCE: 19

Ser Arg Ala Asp Pro Lys Lys Lys Arg Lys Val
1               5                   10

<210> SEQ ID NO 20
<211> LENGTH: 1056
<212> TYPE: PRT
<213> ORGANISM: artificial sequence
<220> FEATURE:
<223> OTHER INFORMATION: amino acid sequence of Cas12f.4-NLS fusion
``` protein

<400> SEQUENCE: 20

Met Lys Lys Val Glu Val Ser Arg Pro Tyr Gln Ser Leu Leu Leu Pro
1               5                   10                  15

Asn His Arg Lys Phe Lys Tyr Leu Asp Glu Thr Trp Asn Ala Tyr Lys
            20                  25                  30

Ser Val Lys Ser Leu Leu His Arg Phe Leu Val Cys Ala Tyr Gly Ala
            35                  40                  45

Val Pro Phe Asn Lys Phe Val Glu Val Val Glu Lys Val Asp Asn Asp
        50                  55                  60

Gln Leu Val Leu Ala Phe Ala Val Arg Leu Phe Arg Leu Val Pro Val
65                  70                  75                  80

Glu Ser Thr Ser Phe Ala Lys Val Asp Lys Ala Asn Leu Ala Lys Ser
                85                  90                  95

Leu Ala Asn His Leu Pro Val Gly Thr Ala Ile Pro Ala Asn Val Gln
            100                 105                 110

Ser Tyr Phe Asp Ser Asn Phe Asp Pro Lys Lys Tyr Met Trp Ile Asp
        115                 120                 125

Cys Ala Trp Glu Ala Asp Arg Leu Ala Arg Glu Met Gly Leu Ser Ala
        130                 135                 140

Ser Gln Phe Ser Glu Tyr Ala Thr Thr Met Leu Trp Glu Asp Trp Leu
145                 150                 155                 160

Pro Leu Asn Lys Asp Asp Val Asn Gly Trp Gly Ser Val Ser Gly Leu
                165                 170                 175

Phe Gly Glu Gly Lys Lys Glu Asp Arg Gln Gln Lys Val Lys Met Leu
            180                 185                 190

Asn Asn Leu Leu Asn Gly Ile Lys Lys Asn Pro Pro Lys Asp Tyr Thr
            195                 200                 205

Gln Tyr Leu Lys Ile Leu Leu Asn Ala Phe Asp Ala Lys Ser His Lys
        210                 215                 220

Glu Ala Val Lys Asn Tyr Lys Gly Asp Ser Thr Gly Arg Thr Ala Ser
225                 230                 235                 240

Tyr Leu Ser Glu Lys Ser Gly Glu Ile Thr Glu Leu Met Leu Glu Gln
                245                 250                 255

Leu Met Ser Asn Ile Gln Arg Asp Ile Gly Asp Lys Gln Lys Glu Ile
            260                 265                 270

Ser Leu Pro Lys Lys Asp Val Val Lys Lys Tyr Leu Glu Ser Glu Ser
        275                 280                 285

Gly Val Pro Tyr Asp Gln Asn Leu Trp Ser Gln Ala Tyr Arg Asn Ala
        290                 295                 300

Ala Ser Ser Ile Lys Lys Thr Asp Thr Arg Asn Phe Asn Ser Thr Leu
305                 310                 315                 320

Glu Lys Phe Lys Asn Glu Val Glu Leu Arg Gly Leu Leu Ser Glu Gly
            325                 330                 335

Asp Asp Val Glu Ile Leu Arg Ser Lys Phe Phe Ser Ser Glu Phe His
            340                 345                 350

Lys Thr Pro Asp Lys Phe Val Ile Lys Pro Glu His Ile Gly Phe Asn
            355                 360                 365

Asn Lys Tyr Asn Val Val Ala Glu Leu Tyr Lys Leu Lys Ala Glu Ala
        370                 375                 380

Thr Asp Phe Glu Ser Ala Phe Ala Thr Val Lys Asp Glu Phe Glu Glu
385                 390                 395                 400

-continued

```
Lys Gly Ile Lys His Pro Ile Lys Asn Ile Leu Glu Tyr Ile Trp Asn
                405             410             415

Asn Glu Val Pro Val Glu Lys Trp Gly Arg Val Ala Arg Phe Asn Gln
            420             425             430

Ser Glu Glu Lys Leu Leu Arg Ile Lys Ala Asn Pro Thr Val Glu Cys
            435             440             445

Asn Gln Gly Met Thr Phe Gly Asn Ser Ala Met Val Gly Glu Val Leu
        450             455             460

Arg Ser Asn Tyr Val Ser Lys Lys Gly Ala Leu Val Ser Gly Glu His
465             470             475             480

Gly Gly Arg Leu Ile Gly Gln Asn Asn Met Ile Trp Leu Glu Met Arg
                485             490             495

Leu Leu Asn Lys Gly Lys Trp Glu Thr His His Val Pro Thr His Asn
            500             505             510

Met Lys Phe Phe Glu Glu Val His Ala Tyr Asn Pro Ser Leu Ala Asp
            515             520             525

Ser Val Asn Val Arg Asn Arg Leu Tyr Arg Ser Glu Asp Tyr Thr Gln
        530             535             540

Leu Pro Ser Ser Ile Thr Asp Gly Leu Lys Gly Asn Pro Lys Ala Lys
545             550             555             560

Leu Leu Lys Arg Gln His Cys Ala Leu Asn Asn Met Thr Ala Asn Val
            565             570             575

Leu Asn Pro Lys Leu Ser Phe Thr Ile Asn Lys Lys Asn Asp Asp Tyr
            580             585             590

Thr Val Ile Ile Val His Ser Val Glu Val Ser Lys Pro Arg Arg Glu
            595             600             605

Val Leu Val Gly Asp Tyr Leu Val Gly Met Asp Gln Asn Gln Thr Ala
        610             615             620

Ser Asn Thr Tyr Ala Val Met Gln Val Val Lys Pro Lys Ser Thr Asp
625             630             635             640

Ala Ile Pro Phe Arg Asn Met Trp Val Arg Phe Val Glu Ser Gly Ser
            645             650             655

Ile Glu Ser Arg Thr Leu Asn Ser Arg Gly Glu Tyr Val Asp Gln Leu
            660             665             670

Asn His Asp Gly Val Asp Leu Phe Glu Ile Gly Asp Thr Glu Trp Val
        675             680             685

Asp Ser Ala Arg Lys Phe Phe Asn Lys Leu Gly Val Lys His Lys Asp
        690             695             700

Gly Thr Leu Val Asp Leu Ser Thr Ala Pro Arg Lys Ala Tyr Ala Phe
705             710             715             720

Asn Asn Phe Tyr Phe Lys Thr Met Leu Asn His Leu Arg Ser Asn Glu
            725             730             735

Val Asp Leu Thr Leu Leu Arg Asn Glu Ile Leu Arg Val Ala Asn Gly
            740             745             750

Arg Phe Ser Pro Met Arg Leu Gly Ser Leu Ser Trp Thr Thr Leu Lys
            755             760             765

Ala Leu Gly Ser Phe Lys Ser Leu Val Leu Ser Tyr Phe Asp Arg Leu
        770             775             780

Gly Ala Lys Glu Met Val Asp Lys Glu Ala Asp Lys Ser Leu Phe
785             790             795             800

Asp Leu Leu Val Ala Ile Asn Asn Lys Arg Ser Asn Lys Arg Glu Glu
            805             810             815

Arg Thr Ser Arg Ile Ala Ser Ser Leu Met Thr Val Ala Gln Lys Tyr
```

```
                   820                 825                 830

Lys Val Asp Asn Ala Val Val His Val Val Val Glu Gly Asn Leu Ser
        835                 840                 845

Ser Thr Asp Arg Ser Ala Ser Lys Ala His Asn Arg Asn Thr Met Asp
        850                 855                 860

Trp Cys Ser Arg Ala Val Val Lys Lys Leu Glu Asp Met Cys Asn Leu
865                 870                 875                 880

Tyr Gly Phe Asn Ile Lys Gly Val Pro Ala Phe Tyr Thr Ser His Gln
                885                 890                 895

Asp Pro Leu Val His Arg Ala Asp Tyr Asp Asp Pro Lys Pro Ala Leu
            900                 905                 910

Arg Cys Arg Tyr Ser Ser Tyr Ser Arg Ala Asp Phe Ser Lys Trp Gly
            915                 920                 925

Gln Asn Ala Leu Ala Ala Val Val Arg Trp Ala Ser Asn Lys Lys Ser
        930                 935                 940

Asn Thr Cys Tyr Lys Val Gly Ala Val Glu Phe Leu Lys Gln His Gly
945                 950                 955                 960

Leu Phe Ala Asp Lys Lys Leu Thr Val Glu Gln Phe Leu Ser Lys Val
                965                 970                 975

Lys Asp Glu Glu Ile Leu Ile Pro Arg Arg Gly Gly Arg Val Phe Leu
            980                 985                 990

Thr Thr His Arg Leu Leu Ala Glu  Ser Thr Phe Val Tyr  Leu Asn Gly
            995                 1000                1005

Val Lys  Tyr His Ser Cys Asn  Ala Asp Glu Val Ala  Ala Val Asn
    1010                1015                1020

Ile Cys  Leu Asn Asp Trp Val  Ile Pro Cys Lys Lys  Lys Met Lys
    1025                1030                1035

Glu Glu  Ser Ser Ala Ser Gly  Ser Arg Ala Asp Pro  Lys Lys Lys
    1040                1045                1050

Arg Lys  Val
    1055
```

```
<210> SEQ ID NO 21
<211> LENGTH: 1090
<212> TYPE: PRT
<213> ORGANISM: artificial sequence
<220> FEATURE:
<223> OTHER INFORMATION: amino acid sequence of Cas12f.5-NLS fusion
      protein

<400> SEQUENCE: 21

Met Pro Lys Gln Lys Asp Leu Pro Tyr Ser Cys Leu Ser Tyr Leu Gln
1               5                   10                  15

Pro Asn Glu Arg Lys Leu Lys Leu Leu Asn Asn Thr Tyr Asp His Leu
            20                  25                  30

Thr His Gly Ser Lys Ile Met Phe Asp Thr Leu Ile Ala Leu Met Gly
        35                  40                  45

Gly Ile Asn Pro Lys Met Asp Val Ile Ser Glu Asn Lys Asp Ser Glu
        50                  55                  60

Ile Lys Asn Asn Arg Asp Pro Gln Thr Met Cys Ala Thr Ile Trp Phe
65                  70                  75                  80

Arg Pro Met Lys Ser Lys Arg Ile Asn Lys Val Trp Ser Pro Lys Gln
                85                  90                  95

Leu Lys Glu Gln Phe Leu Lys Tyr Tyr Gln Glu Tyr Glu Ala Asp Val
            100                 105                 110
```

-continued

```
Lys Ile Asn Asp Met Val Glu Ala Tyr Phe Asp Ser Pro Leu Gly Glu
        115                 120                 125

Asn Tyr Val Trp Val Asp Cys Arg Lys Lys Tyr Lys Gln Leu Val Lys
        130                 135                 140

Glu Leu Ala Ser Ile Ala Lys Thr Thr Glu Ala Asn Leu Lys Glu Asp
145                 150                 155                 160

Leu Asp Cys Asp Leu Glu Cys Leu Phe Arg Pro Ser Glu Lys Lys Met
                165                 170                 175

Lys Leu Tyr Gly Ser Asn Lys Ser Trp Ala Ile Ile Ser Asn Leu Phe
            180                 185                 190

Gly Glu Gly Asp Lys Glu Asp Arg Ser Lys Lys Ile Lys Ile Leu Thr
            195                 200                 205

Lys Ala Ile Gln Ile Leu Thr Glu Ser Asn Pro Glu Ser Tyr Ala Asp
        210                 215                 220

Val Gln Lys Ala Phe Leu Ala Ala Ala Asp Ile Asp Asp Pro Lys Lys
225                 230                 235                 240

Phe His Thr Gln Glu Ile Trp Gly Asn Gly Ser Pro Gly Asn Ile Val
                245                 250                 255

Lys Met Ala Arg Gly Asp Phe Leu Gly Lys Glu Phe Asp Cys Glu Lys
            260                 265                 270

Ile Leu Glu Lys Ile Asn Asp Val Leu Lys Glu Lys Thr Leu Asp Phe
        275                 280                 285

Asp Leu Lys Val Arg Leu Ser Phe Lys Glu Tyr Leu Ile Ser Lys Ile
        290                 295                 300

Gly His Tyr Tyr Gln Asn Ser Trp Ser Glu Met Ile Asn Ser Ala Phe
305                 310                 315                 320

Ala Asp Ile Ile Ser Lys Asn Thr Arg Asn Val Asn Phe Ala Lys Glu
                325                 330                 335

Lys Val Gln Leu Gln Lys Thr Leu Ser Glu Thr Ser Asn Ala Lys Val
            340                 345                 350

Glu Leu Leu Thr Asp Phe Phe Lys Ser Asp Phe Phe Leu Gly Asp Asp
            355                 360                 365

Lys Phe Asp Ile Ala Pro His Asn Leu Gly Gly Ala Asn Gly Ile Lys
        370                 375                 380

Phe Phe Tyr Asp Phe Cys Lys Lys Asn Glu Asp Gln Tyr Phe Leu Glu
385                 390                 395                 400

Glu Leu Leu Leu Glu Ala Ala Ile Glu Glu Ser Val Ala Glu Ala Lys
                405                 410                 415

Ser Lys Ser Leu Lys Glu Pro His Lys Asp Leu Leu Arg Tyr Val Phe
            420                 425                 430

Ser Ile Arg Lys Glu Thr Thr Phe Glu Glu Leu Arg Asp Ala Ala Lys
            435                 440                 445

Tyr Ile Gln Thr His Lys Arg Ile Lys Asn Met Ser Val His Pro Thr
        450                 455                 460

Val Lys Ser Asp Ile Gly Phe Asn Val Thr Ser Gly Ser Ala Leu Val
465                 470                 475                 480

Gly His Val Val Ser Pro Ser Lys Lys Ile Asn Gly Arg Ile Ala Gly
                485                 490                 495

Glu Ser Gly Phe Ile Trp Ile Cys Met Lys Leu Trp Glu Gly Gly Asp
            500                 505                 510

Lys Trp Ile Glu His His Ile Pro Phe Thr Asp Thr Arg Phe Tyr Glu
            515                 520                 525

Gln Ile Tyr Lys Tyr Asn Pro Asp Ser Lys Leu Glu Pro Val Val Leu
```

```
        530             535             540

Arg Thr Lys Arg Tyr Gly Val Asp Leu Thr Lys Phe Asn Leu Pro Pro
545             550             555             560

Met Lys Thr Asp Leu Lys His Val Ala Pro Lys Glu Lys Asn Lys His
                565             570             575

Asn Tyr Val Lys Val Gln Arg Arg Leu Gln Arg Leu Asn His Pro Asp
                580             585             590

Val Pro Asn Thr Ile Trp Pro Lys Ser Asn Ile Gly Phe Thr Ile Arg
                595             600             605

Arg Lys Asn Gly Lys Tyr Ile Leu Asn Val Val His Lys Leu Pro Lys
            610             615             620

Asn Lys Val Lys Lys Ser Val Lys Pro Lys Phe Gly Asp Ile Leu Ile
625             630             635             640

Gly Val Asp Gln Asn Gln Thr Thr Asn His Thr Cys Ser Ile Tyr Lys
                645             650             655

Val Val Lys Lys Asn Thr Lys Glu Ala Leu Leu Val Pro Glu Ser Asp
                660             665             670

Phe Tyr Leu Lys Lys Ile Glu Thr Ile Lys Val Thr Ser Phe Thr Lys
                675             680             685

Ala Arg Tyr Asn Ser Glu Pro Ile Asp Gln Leu His Tyr Glu Gly Ile
            690             695             700

Ser Val Asp Asn Glu Val Phe Lys Asn Trp Cys Lys Asp Arg Glu Gln
705             710             715             720

Phe Val Asp Ser Leu Ser Ile Lys Glu Phe Lys Asn Glu Phe Lys Arg
                725             730             735

Ile Lys Asn Lys Asn Glu Asn Leu Tyr Ser Phe Asn Ala Asp Tyr Leu
                740             745             750

Trp Leu Leu Lys Arg Ile Ile Ser Gly Lys Leu Asn Lys Lys Lys Phe
                755             760             765

Asp Val Ser Val Phe Glu Lys Ser Ile Arg Asn Glu Ile Leu Ala Met
            770             775             780

Cys Ser Lys Glu Gly Leu Gly Pro Leu Arg Val Ser Ser Leu Ser Ser
785             790             795             800

Asn Ser Leu Lys Ser Ile Gly Phe Leu Lys Ser Ala Ile Cys Ser Phe
                805             810             815

Ile Ser Ile Ala Leu Asn Arg Lys Gly Ile Glu Asp Lys Thr Asp Val
                820             825             830

Gln Lys Asn Lys Ile Asp Pro Glu Leu Phe Asp Leu Ile Gly Lys Ile
                835             840             845

Glu Gln Lys Arg Val Asn Lys Arg Met Glu Lys Thr Arg Arg Asn Ala
            850             855             860

Asp Phe Ile Leu Thr Met Ala Val Asp Tyr Gln Lys Ser Ser Gln Lys
865             870             875             880

Asn Val Phe Leu Phe Cys Glu Gly Asn Leu Glu Thr Ala Lys Thr Gly
                885             890             895

Asn Ser Lys Lys Arg Asn Ser Ala Asn Val Asp Trp Cys Ser Arg Lys
                900             905             910

Leu Phe Asp Phe Leu Lys Glu Lys Ser Leu Arg His Gly Ile Tyr Phe
                915             920             925

His Ala Val Thr Pro His Tyr Thr Ser His Gln Asp Pro Phe Glu Tyr
            930             935             940

His Pro Ser Asn Lys Val Met Leu Pro Arg Phe Ala Lys Phe Asp Lys
945             950             955             960
```

-continued

```
Asn Asn Pro Ile Gln Asp Trp Ala Glu Lys Lys Tyr Leu Gly Phe Ala
            965                 970                 975

Asn Ser Asp Pro Glu Ser Gly Thr Ala Leu Tyr Tyr Lys Lys Gly Val
            980                 985                 990

Glu Asn Phe Phe Ala His Tyr Gln Lys Gly Phe Lys Glu Lys Val Glu
            995                 1000                1005

Leu Ala Glu Met Lys Asn Val Leu Asn Ser Asn Leu Lys Asn Gly
            1010                1015            1020

Asn Leu Glu His Val Phe Cys Pro Ile Arg Gly Gly Arg Tyr Tyr
            1025                1030            1035

Leu Ser Thr His Pro Val Thr Ser Asp Ala Lys Pro Phe Glu Phe
            1040                1045            1050

Asn Gly Arg Lys Cys Tyr Ile Cys Asp Ser Asp Glu Val Ala Ala
            1055                1060            1065

Thr Asn Ile Met Leu Ile Gly Leu Phe Tyr Val Ser Arg Ala Asp
            1070                1075            1080

Pro Lys Lys Lys Arg Lys Val
            1085                1090

<210> SEQ ID NO 22
<211> LENGTH: 1065
<212> TYPE: PRT
<213> ORGANISM: artificial sequence
<220> FEATURE:
<223> OTHER INFORMATION: amino acid sequence of Cas12f.6-NLS fusion
      protein

<400> SEQUENCE: 22

Met Ser Ser Ala Ile Lys Ser Tyr Lys Ser Val Leu Arg Pro Asn Glu
1               5                   10                  15

Arg Lys Asn Gln Leu Leu Lys Ser Thr Ile Gln Cys Leu Glu Asp Gly
            20                  25                  30

Ser Ala Phe Phe Phe Lys Met Leu Gln Gly Leu Phe Gly Gly Ile Thr
            35                  40                  45

Pro Glu Ile Val Arg Phe Ser Thr Glu Gln Glu Lys Gln Gln Gln Asp
        50                  55                  60

Ile Ala Leu Trp Cys Ala Val Asn Trp Phe Arg Pro Val Ser Gln Asp
65                  70                  75                  80

Ser Leu Thr His Thr Ile Ala Ser Asp Asn Leu Val Glu Lys Phe Glu
                85                  90                  95

Glu Tyr Tyr Gly Gly Thr Ala Ser Asp Ala Ile Lys Gln Tyr Phe Ser
            100                 105                 110

Ala Ser Ile Gly Glu Ser Tyr Tyr Trp Asn Asp Cys Arg Gln Gln Tyr
            115                 120                 125

Tyr Asp Leu Cys Arg Glu Leu Gly Val Glu Val Ser Asp Leu Thr His
            130                 135                 140

Asp Leu Glu Ile Leu Cys Arg Glu Lys Cys Leu Ala Val Ala Thr Glu
145                 150                 155                 160

Ser Asn Gln Asn Asn Ser Ile Ile Ser Val Leu Phe Gly Thr Gly Glu
                165                 170                 175

Lys Glu Asp Arg Ser Val Lys Leu Arg Ile Thr Lys Lys Ile Leu Glu
            180                 185                 190

Ala Ile Ser Asn Leu Lys Glu Ile Pro Lys Asn Val Ala Pro Ile Gln
            195                 200                 205

Glu Ile Ile Leu Asn Val Ala Lys Ala Thr Lys Glu Thr Phe Arg Gln
```

-continued

```
               210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
                260                 265                 270

Gln Glu Glu Leu Arg Ser Tyr Val Glu Gln Asn Thr Ile Gln Tyr Asp
                275                 280                 285

Leu Trp Ala Trp Gly Glu Met Phe Asn Lys Ala His Thr Ala Leu Lys
                290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
                325                 330                 335

Asn Asp Phe Phe Asp Ser Glu Phe Phe Ser Gly Glu Glu Thr Tyr Thr
                340                 345                 350

Ile Cys Val His His Leu Gly Gly Lys Asp Leu Ser Lys Leu Tyr Lys
                355                 360                 365

Ala Trp Glu Asp Asp Pro Ala Asp Pro Glu Asn Ala Ile Val Val Leu
370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
                420                 425                 430

Lys Ala Asn Pro Ser Val Leu Gly Asn Gln Gly Phe Thr Trp Thr Asn
                435                 440                 445

Ala Val Ile Leu Pro Glu Lys Ala Gln Arg Asn Asp Arg Pro Asn Ser
                450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
                500                 505                 510

Thr Pro Arg Phe Gly Tyr His Leu Pro Lys Leu Thr Asp Gln Thr Ala
                515                 520                 525

Ile Arg Val Asn Lys Lys His Val Lys Ala Ala Lys Thr Glu Ala Arg
                530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Asp Val Gly Arg Gln Lys Gly Thr Leu Gln Ile Gly
                580                 585                 590

Asp Arg Phe Cys Gly Tyr Asp Gln Asn Gln Thr Ala Ser His Ala Tyr
                595                 600                 605

Ser Leu Trp Glu Val Val Lys Glu Gly Gln Tyr His Lys Glu Leu Gly
                610                 615                 620

Cys Phe Val Arg Phe Ile Ser Ser Gly Asp Ile Val Ser Ile Thr Glu
625                 630                 635                 640
```

-continued

```
Asn Arg Gly Asn Gln Phe Asp Gln Leu Ser Tyr Glu Gly Leu Ala Tyr
            645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
            675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750

Thr Leu Glu Thr Val Lys Ala Val Lys Gly Ile Ile Tyr Ser Tyr Phe
            755                 760                 765

Ser Thr Ala Leu Asn Ala Ser Lys Asn Asn Pro Ile Ser Asp Glu Gln
    770                 775                 780

Arg Lys Glu Phe Asp Pro Glu Leu Phe Ala Leu Leu Glu Lys Leu Glu
785                 790                 795                 800

Leu Ile Arg Thr Arg Lys Lys Lys Gln Lys Val Glu Arg Ile Ala Asn
                805                 810                 815

Ser Leu Ile Gln Thr Cys Leu Glu Asn Asn Ile Lys Phe Ile Arg Gly
            820                 825                 830

Glu Gly Asp Leu Ser Thr Thr Asn Asn Ala Thr Lys Lys Lys Ala Asn
            835                 840                 845

Ser Arg Ser Met Asp Trp Leu Ala Arg Gly Val Phe Asn Lys Ile Arg
    850                 855                 860

Gln Leu Ala Pro Met His Asn Ile Thr Leu Phe Gly Cys Gly Ser Leu
865                 870                 875                 880

Tyr Thr Ser His Gln Asp Pro Leu Val His Arg Asn Pro Asp Lys Ala
                885                 890                 895

Met Lys Cys Arg Trp Ala Ala Ile Pro Val Lys Asp Ile Gly Asp Trp
            900                 905                 910

Val Leu Arg Lys Leu Ser Gln Asn Leu Arg Ala Lys Asn Ile Gly Thr
            915                 920                 925

Gly Glu Tyr Tyr His Gln Gly Val Lys Glu Phe Leu Ser His Tyr Glu
    930                 935                 940

Leu Gln Asp Leu Glu Glu Glu Leu Leu Lys Trp Arg Ser Asp Arg Lys
945                 950                 955                 960

Ser Asn Ile Pro Cys Trp Val Leu Gln Asn Arg Leu Ala Glu Lys Leu
                965                 970                 975

Gly Asn Lys Glu Ala Val Val Tyr Ile Pro Val Arg Gly Gly Arg Ile
            980                 985                 990

Tyr Phe Ala Thr His Lys Val Ala  Thr Gly Ala Val Ser  Ile Val Phe
    995                 1000                1005

Asp Gln Lys Gln Val Trp Val  Cys Asn Ala Asp His  Val Ala Ala
    1010                1015                1020

Ala Asn Ile Ala Leu Thr Val  Lys Gly Ile Gly Glu  Gln Ser Ser
    1025                1030                1035

Asp Glu Glu Asn Pro Asp Gly  Ser Arg Ile Lys Leu  Gln Leu Thr
    1040                1045                1050
```

-continued

```
Ser Ser  Arg Ala Asp Pro Lys  Lys Lys Arg Lys Val
    1055              1060                  1065

<210> SEQ ID NO 23
<211> LENGTH: 3713
<212> TYPE: DNA
<213> ORGANISM: artificial sequence
<220> FEATURE:
<223> OTHER INFORMATION: Plasmid expressing Cas12f.4 system

<400> SEQUENCE: 23
tttacacttt atgcttccgg ctcgtatgtt aggaggtctt tatcatgtct aacaaagaaa      60
aaaatgcaag cgaaactcgc aaagcctaca caacaaaaat gattccaaga agccatgatc     120
gcatgaaatt gcttgggaat ttcatggatt atttgatgga tggaacgcca atattttttcg    180 aactttggaa tcagtttggc ggcgggattg accgcgatat catttctggc actgcaaata     240
aagacaagat atcagatgat ttacttttgg cggtcaattg gttcaaggta atgccaatta     300
attctaagcc tcaaggtgta tcgccatcaa atcttgccaa cctctttcaa caatactctg     360
gatcagaacc agacattcaa gctcaagagt attttgcttc aaattttgac accgaaaagc     420
atcaatggaa ggacatgcgt gttgaatacg aacgactatt agctgaattg cagctatcga     480
gaagtgatat gcatcatgac ttgaagctca tgtacaaaga aaaatgcatt ggcctaagtc     540
tttctacggc tcactacatc acttctgtga tgtttgggac aggagctaaa aacaatcgcc     600
aaaccaagca tcaattctat agcaaggtta tccaactact tgaggaatca actcaaatca     660
attctgttga acagttggca tctattattt tgaaagcagg agattgcgat agttatcgaa     720
agcttcgtat tcgatgttct cgtaagggag caacacccag cattcttaag atcgttcaag     780
actatgaact gggaaccaat cacgatgatg aagtgaatgt gccaagtttg attgcaaatt     840
tgaaagaaaa attgggcaga tttgaatatg aatgcgaatg gaagtgcatg gaaaaaatca     900
aagcattttt agctagcaaa gttgggcctt attcctagg ctcttacagt gcgatgcttg      960
aaaatgcatt gtcgcccatc aagggaatga ctacaaaaaa ttgcaaattt gtgttaaagc    1020
aaattgatgc caaaaacgac atcaagtatg aaaatgagcc atttggcaaa attgttgaag    1080
ggttttttga ctctccatat tttgaaagcg acaccaatgt gaaatgggtt ttgcacccac    1140
atcatattgg agaaagcaat atcaaaacac tctgggaaga cttgaatgca attcattcta    1200
agtacgaaga agatattgct tctttgagcg aagacaaaaa agagaaacgc attaaggttt    1260
atcaaggaga tgtttgccaa acaatcaata cgtattgtga agaagtagga aaggaagcta    1320
agactccttt agttcagctt ttgcgttatc tttactctag aaaagatgat attgctgttg    1380
ataagataat tgatggcatt accttcctta gcaagaaaca caaggttgaa aaacaaaaaa    1440
tcaatcctgt aattcaaaaa tatcccagtt tcaactttgg gaataattct aagttgttgg    1500
gaaagattat cagccccaaa gacaagttaa agcataatct caaatgcaac aggaatcagg    1560
ttgataatta catttggatt gagattaaag tactaaacac caaaacgatg cgatgggaaa    1620
agcatcacta tgctttatca tctacgcggt ttttggaaga ggtctattat ccagccacat    1680
ccgaaaatcc gccagacgct ttggcagcac gtttccgaac taaaactaat gggtatgaag    1740
gcaagcctgc gttgtctgct gagcaaattg aacaaattag atcagcccca gtcggtttga    1800
gaaaagtgaa aaaacgtcaa atgcgactcg aagctgcaag acagcaaaat ctcttgcctc    1860
gatacacttg gggcaaagat ttcaacataa acatttgtaa gcgtggcaac aattttgaag    1920
tcactcttgc gacgaaggtg aaaaagaaaa agaaaagaa ttataaggtt gttttagggt    1980
```

-continued

```
acgatgctaa tatcgttcgc aaaaacactt acgcagccat agaagctcac gctaatggcg      2040
atggtgtgat tgactacaat gacttgcccg tgaagcctat tgaaagtgga tttgtaaccg      2100
ttgaaagtca agtgcgagac aaatcttacg atcaactctc ttacaatggc gtaaagctct      2160
tgtattgcaa gcctcatgtt gagtctcgac gttcattttt ggagaaatac cgaaatggca      2220
ccatgaagga caacagagga aacaacattc aaattgactt tatgaaagac tttgaagcta      2280
ttgcggatga tgaaacttct ttgtattact tcaatatgaa gtactgcaag ctgcttcaat      2340
cgtccattcg caatcattct tcacaagcaa aagaatatcg tgaagagatt tttgaattgt      2400
taagagacgg aaaactatcg gttttgaagt tatcatcttt gagcaatctt tcttttgtga      2460
tgttcaaagt tgccaaatct ctgatcggta cttactttgg ccacttgctt aagaagccga      2520
agaattctaa gtcagatgtt aaggcaccgc ctataactga tgaagataag caaaaagctg      2580
atcctgagat gtttgctttg aggttggctt tggaggagaa gcgactaaac aaagtcaagt      2640
ctaagaaaga agtaattgcg aacaagattg ttgctaaggc acttgagctt cgcgacaagt      2700
acgggcctgt gttgattaag ggagaaaaca tctctgacac gaccaagaaa ggcaagaagt      2760
caagcaccaa ttctttttttg atggactggc tagcacgcgg tgtggctaat aaagtcaaag      2820
aaatggtaat gatgcatcaa ggacttgaat ttgtagaagt aaatcctaat ttcacatctc      2880
accaagatcc ttttgttcac aagaaccctg aaaatacgtt tagagctagg tacagtcggt      2940
gcactccaag tgaacttact gagaaaaatc gcaaggaaat tttgagcttt ttgagcgata      3000
agccttctaa acgaccgaca aatgcctatt acaatgaagg tgcgatggcc tttcttgcaa      3060
cttatggctt gaagaagaat gatgtgctag gagttagtct tgagaaattc aagcaaataa      3120
tggccaacat tctacatcag cgttccgaag atcaattatt gtttccttct agaggtggca      3180
tgttttatct tgcaacttac aagcttgatg ctgacgctac ctctgtaaat tggaatggca      3240
aacagttttg ggtttgtaac gcagatttag tagcggcata caatgtcggt ttggtcgata      3300
ttcaaaaaga cttcaagaaa aagtaaaaat aaaacgaaag gctcagtcga aagactgggc      3360
ctttcgtttt atctgttgtt tgtcggtgaa cgctctcctg agtaggacaa atttgacagc      3420
tagctcagtc ctaggtataa tgctagcgct gacgttggaa tgactaattt ttgtgcccac      3480
cgttggcacg gtataacaac ttcgacgagc tctacacgtt ggaatgacta atttttgtgc      3540
ccaccgttgg cacggatcgc tgagaccgca tcaaagcacg atgagcgtgg cgttggaatg      3600
actaattttt gtgcccaccg ttggcacaaa taaaacgaaa ggctcagtcg aaagactggg      3660
cctttcgttt tatctgttgt ttgtcggtga acgctctcct gagtaggaca aat          3713
```

```
<210> SEQ ID NO 24
<211> LENGTH: 35
<212> TYPE: DNA
<213> ORGANISM: artificial sequence
<220> FEATURE:
<223> OTHER INFORMATION: PAM library sequence
<220> FEATURE:
<221> NAME/KEY: misc_feature
<222> LOCATION: (1)..(8)
<223> OTHER INFORMATION: n = a or g or c or t

<400> SEQUENCE: 24
nnnnnnnngg tataacaact tcgacgagct ctaca                                35

<210> SEQ ID NO 25
<211> LENGTH: 43
<212> TYPE: RNA
<213> ORGANISM: artificial sequence
```

-continued

<220> FEATURE:
<223> OTHER INFORMATION: Guide RNA-VEGFA of Cas12f.4 system

<400> SEQUENCE: 25
agagaaugug ugcauaguca caccuaggaa uauugaaggg ggc                    43

<210> SEQ ID NO 26
<211> LENGTH: 44
<212> TYPE: RNA
<213> ORGANISM: artificial sequence
<220> FEATURE:
<223> OTHER INFORMATION: Guide RNA-VEGFA of Cas12f.5 system

<400> SEQUENCE: 26
agaaaaugug ucauacuacg acaccuagga auauugaagg gggc                   44

<210> SEQ ID NO 27
<211> LENGTH: 43
<212> TYPE: RNA
<213> ORGANISM: artificial sequence
<220> FEATURE:
<223> OTHER INFORMATION: Guide RNA-VEGFA of Cas12f.6 system

<400> SEQUENCE: 27
agaaauccgu cuuucauuga cggcuaggaa uauugaaggg ggc                    43

<210> SEQ ID NO 28
<211> LENGTH: 44
<212> TYPE: RNA
<213> ORGANISM: artificial sequence
<220> FEATURE:
<223> OTHER INFORMATION: Guide RNA-PDI1 of Cas12f.4 system

<400> SEQUENCE: 28
agagaaugug ugcauaguca cacccuuguc cuugaauucc uccg                   44

<210> SEQ ID NO 29
<211> LENGTH: 44
<212> TYPE: RNA
<213> ORGANISM: artificial sequence
<220> FEATURE:
<223> OTHER INFORMATION: Guide RNA-SBE2.2 of Cas12f.4 system

<400> SEQUENCE: 29
agagaaugug ugcauaguca caccggugga uuuagucggc uuga                   44

<210> SEQ ID NO 30
<211> LENGTH: 40
<212> TYPE: DNA
<213> ORGANISM: artificial sequence
<220> FEATURE:
<223> OTHER INFORMATION: PAM-VEGFA Target

<400> SEQUENCE: 30
tccctctttg ctaggaatat tgaagggggc aggggaaggc                        40

<210> SEQ ID NO 31
<211> LENGTH: 40
<212> TYPE: DNA
<213> ORGANISM: artificial Sequence
<220> FEATURE:
<223> OTHER INFORMATION: PAM-VEGFA Target

<400> SEQUENCE: 31
gccttcccct gccccccttca atattcctag caaagaggga                       40

```
<210> SEQ ID NO 32
<211> LENGTH: 43
<212> TYPE: DNA
<213> ORGANISM: artificial sequence
<220> FEATURE:
<223> OTHER INFORMATION: crRNA Cas12f.4

<400> SEQUENCE: 32
agagaaugug ugcauaguca cacctaggaa tattgaaggg ggc                         43

<210> SEQ ID NO 33
<211> LENGTH: 32
<212> TYPE: DNA
<213> ORGANISM: artificial sequence
<220> FEATURE:
<223> OTHER INFORMATION: result of cleavage activity PAM-VEGFA Target

<400> SEQUENCE: 33
tccctctttg ctaggaatat tgaggggaag gc                                     32

<210> SEQ ID NO 34
<211> LENGTH: 31
<212> TYPE: DNA
<213> ORGANISM: artificial sequence
<220> FEATURE:
<223> OTHER INFORMATION: result of cleavage activity PAM-VEGFA Target

<400> SEQUENCE: 34
tccctctttg ctaggaatat tgaaggaagg c                                      31

<210> SEQ ID NO 35
<211> LENGTH: 32
<212> TYPE: DNA
<213> ORGANISM: artificial sequence
<220> FEATURE:
<223> OTHER INFORMATION: result of cleavage activity PAM-VEGFA Target

<400> SEQUENCE: 35
tccctctttg ctaggaatat tgaagggaag gc                                     32

<210> SEQ ID NO 36
<211> LENGTH: 39
<212> TYPE: DNA
<213> ORGANISM: artificial sequence
<220> FEATURE:
<223> OTHER INFORMATION: result of cleavage activity PAM-VEGFA Target

<400> SEQUENCE: 36
tccctctttg ctaggaatat tgaagggggc agggaaggc                              39

<210> SEQ ID NO 37
<211> LENGTH: 25
<212> TYPE: DNA
<213> ORGANISM: artificial sequence
<220> FEATURE:
<223> OTHER INFORMATION: result of cleavage activity PAM-VEGFA Target

<400> SEQUENCE: 37
tccctctttg ctaggaatag aaggc                                             25

<210> SEQ ID NO 38
<211> LENGTH: 47
<212> TYPE: DNA
<213> ORGANISM: artificial sequence
<220> FEATURE:
<223> OTHER INFORMATION: PDI1 target
```

<400> SEQUENCE: 38
cttgatttcc ttgtccttga attcctccgc ggcagcagag taggcag          47

<210> SEQ ID NO 39
<211> LENGTH: 35
<212> TYPE: DNA
<213> ORGANISM: artificial sequence
<220> FEATURE:
<223> OTHER INFORMATION: result of cleavage activity PDI1 target

<400> SEQUENCE: 39
cttgatttcc ttgtccttga cagcagagta ggcag          35

<210> SEQ ID NO 40
<211> LENGTH: 38
<212> TYPE: DNA
<213> ORGANISM: artificial sequence
<220> FEATURE:
<223> OTHER INFORMATION: result of cleavage activity PDI1 target

<400> SEQUENCE: 40
cttgatttcc ttgtccttga attcagcaga gtaggcag          38

<210> SEQ ID NO 41
<211> LENGTH: 41
<212> TYPE: DNA
<213> ORGANISM: artificial sequence
<220> FEATURE:
<223> OTHER INFORMATION: result of cleavage activity PDI1 target

<400> SEQUENCE: 41
cttgatttcc ttgtccttga attcggcagc agagtaggca g          41

<210> SEQ ID NO 42
<211> LENGTH: 44
<212> TYPE: DNA
<213> ORGANISM: artificial sequence
<220> FEATURE:
<223> OTHER INFORMATION: result of cleavage activity PDI1 target

<400> SEQUENCE: 42
cttgatttcc ttgtccttga attccgcggc agcagagtag gcag          44

<210> SEQ ID NO 43
<211> LENGTH: 32
<212> TYPE: DNA
<213> ORGANISM: artificial sequence
<220> FEATURE:
<223> OTHER INFORMATION: result of cleavage activity PDI1 target

<400> SEQUENCE: 43
cttgatttcc ttgtccttga aagagtaggc ag          32

<210> SEQ ID NO 44
<211> LENGTH: 31
<212> TYPE: DNA
<213> ORGANISM: artificial sequence
<220> FEATURE:
<223> OTHER INFORMATION: result of cleavage activity PDI1 target

<400> SEQUENCE: 44
cttgatttcc ttgtccttga agagtaggca g          31

<210> SEQ ID NO 45

-continued

```
<211> LENGTH: 27
<212> TYPE: DNA
<213> ORGANISM: artificial sequence
<220> FEATURE:
<223> OTHER INFORMATION: result of cleavage activity PDI1 target

<400> SEQUENCE: 45
cttgatttcc ttgtgcagag taggcag                                        27

<210> SEQ ID NO 46
<211> LENGTH: 34
<212> TYPE: DNA
<213> ORGANISM: artificial sequence
<220> FEATURE:
<223> OTHER INFORMATION: result of cleavage activity PDI1 target

<400> SEQUENCE: 46
cttgatttcc ttgtccttga agcagagtag gcag                                34

<210> SEQ ID NO 47
<211> LENGTH: 29
<212> TYPE: DNA
<213> ORGANISM: artificial sequence
<220> FEATURE:
<223> OTHER INFORMATION: result of cleavage activity PDI1 target

<400> SEQUENCE: 47
cttgatttcc ttgtccttag agtaggcag                                      29

<210> SEQ ID NO 48
<211> LENGTH: 47
<212> TYPE: DNA
<213> ORGANISM: artificial sequence
<220> FEATURE:
<223> OTHER INFORMATION: SBE2.2 target

<400> SEQUENCE: 48
ggccttttcg gtggatttag tcggcttgat catgatgccg agtactt                  47

<210> SEQ ID NO 49
<211> LENGTH: 36
<212> TYPE: DNA
<213> ORGANISM: artificial sequence
<220> FEATURE:
<223> OTHER INFORMATION: result of cleavage activity SBE2.2 target

<400> SEQUENCE: 49
ggccttttcg gtggatttag tcgatgccga gtactt                              36

<210> SEQ ID NO 50
<211> LENGTH: 36
<212> TYPE: DNA
<213> ORGANISM: artificial sequence
<220> FEATURE:
<223> OTHER INFORMATION: result of cleavage activity SBE2.2 target

<400> SEQUENCE: 50
ggccttttcg gtggatttag tcgatgccga gtactt                              36

<210> SEQ ID NO 51
<211> LENGTH: 35
<212> TYPE: DNA
<213> ORGANISM: artificial sequence
<220> FEATURE:
<223> OTHER INFORMATION: result of cleavage activity SBE2.2 target

<400> SEQUENCE: 51
```

-continued

```
ggccttttcg gtggatttaa tgatgccgag tactt                                    35

<210> SEQ ID NO 52
<211> LENGTH: 35
<212> TYPE: DNA
<213> ORGANISM: artificial sequence
<220> FEATURE:
<223> OTHER INFORMATION: result of cleavage activity SBE2.2 target

<400> SEQUENCE: 52
ggccttttcg gtggatttag tcatgccgag tactt                                    35

<210> SEQ ID NO 53
<211> LENGTH: 33
<212> TYPE: DNA
<213> ORGANISM: artificial sequence
<220> FEATURE:
<223> OTHER INFORMATION: result of cleavage activity SBE2.2 target

<400> SEQUENCE: 53
ggccttttcg gtggatttaa atgccgagta ctt                                      33

<210> SEQ ID NO 54
<211> LENGTH: 29
<212> TYPE: DNA
<213> ORGANISM: artificial sequence
<220> FEATURE:
<223> OTHER INFORMATION: result of cleavage activity SBE2.2 target

<400> SEQUENCE: 54
ggccttttcg gtggatttgc cgagtactt                                           29
```